US009169203B2

(12) United States Patent
Grady et al.

(10) Patent No.: US 9,169,203 B2
(45) Date of Patent: Oct. 27, 2015

(54) SULFOXIDE-BASED SURFACTANTS

(71) Applicants: Novus International Inc., St. Charles, MO (US); Board of Regents of the University of Oklahoma, Norman, OK (US)

(72) Inventors: Brian Grady, Norman, OK (US); Jeff Harwell, Norman, OK (US); Graciela Arhancet, St. Charles, MO (US); Scott Long, St. Charles, MO (US); Richard Vonder Embse, St. Charles, MO (US); Guangzhe Yu, Norman, OK (US)

(73) Assignee: Novus International, Inc., St. Charles, MO (US)

( * ) Notice: Subject to any disclaimer, the term of this patent is extended or adjusted under 35 U.S.C. 154(b) by 28 days.

(21) Appl. No.: 13/729,226

(22) Filed: Dec. 28, 2012

(65) Prior Publication Data

US 2013/0178540 A1   Jul. 11, 2013

Related U.S. Application Data

(60) Provisional application No. 61/583,809, filed on Jan. 6, 2012.

(51) Int. Cl.
*C07C 317/46* (2006.01)
*C07C 317/48* (2006.01)
*C11D 1/00* (2006.01)
*C11D 1/755* (2006.01)

(52) U.S. Cl.
CPC ............. *C07C 317/46* (2013.01); *C07C 317/48* (2013.01); *C11D 1/002* (2013.01); *C11D 1/755* (2013.01)

(58) Field of Classification Search
None
See application file for complete search history.

(56) References Cited

U.S. PATENT DOCUMENTS

| | | | |
|---|---|---|---|
| 2,787,595 A | 4/1957 | Webb | |
| 3,288,859 A | 11/1966 | Lyness et al. | |
| 3,290,254 A | 12/1966 | Anderson | |
| 3,329,617 A | 7/1967 | Doering | |
| 3,761,518 A | 9/1973 | Haglid | |
| 4,095,029 A | 6/1978 | Fields | |
| 4,317,779 A | 3/1982 | Crawford | |
| 4,395,363 A | 7/1983 | Crawford | |
| 4,720,484 A | 1/1988 | Vincent et al. | |
| 5,294,605 A | 3/1994 | Houghten et al. | |
| 5,357,001 A | 10/1994 | Grosse-Bley et al. | |
| 5,602,229 A | 2/1997 | Malabarba et al. | |
| 6,008,261 A * | 12/1999 | Genova et al. | 516/58 |
| 6,172,067 B1 | 1/2001 | Ito et al. | |
| 6,180,643 B1 | 1/2001 | Zablocki et al. | |
| 6,518,243 B1 | 2/2003 | Kahne et al. | |
| 7,250,443 B2 | 7/2007 | Desai et al. | |
| 7,381,416 B2 | 6/2008 | Erdelmeir | |
| 2009/0200511 A1 | 8/2009 | Allen et al. | |

FOREIGN PATENT DOCUMENTS

| | | | |
|---|---|---|---|
| WO | 2005077882 | | 8/2005 |
| WO | 2010082175 | * | 1/2010 |
| WO | 2010/126794 A1 | | 11/2010 |
| WO | 2013103598 A2 | | 7/2013 |
| WO | 2013119959 | | 8/2013 |

OTHER PUBLICATIONS

Balg et al., "Inhibition of Helicobacter pylori Aminoacyl-tRNA Amidotransferase by Puromycin Analogues", J. Am. Chem. Soc., 2008, pp. 3264-3265, vol. 130, No. 11.
Clint et al., "Thermodynamics of Micellization of Homologous Series of n-Alkyl Methyl Sulphoxides and n-Alkyl (dimethyl)phospine Oxides", J. Chem. Soc., Faraday Transactions 1, 1975, pp. 946-954, vol. 71.
Clint, "Micellization of Mixed Nonionic Surface Active Agents", J. Chem. Soc., Faraday Transactions 1, 1975, pp. 1327-1334, vol. 71.
Evans et al., "Nanomolar-Affinity, Non-Peptide Oxytocin Receptor Antagonists", Journal of Medicinal Chemistry, 1993, pp. 3993-4005, vol. 36, No. 25.
Hennaux et al., "Novel nonionic polymerisable surfactants based on sulfoxides. 1. Monomer synthesis and general surfactant behaviour", Colloid Polym. Sci., 2001, pp. 1149-1159, vol. 279.
Hennaux et al., "Novel nonionic surfactants based on sulfoxides. 2. Homo- and copolymers", Colloid Polym. Sci., 2003, pp. 807-814, vol. 281.
Ignasiak et al., "Characterization by mass spectrometry and IRMPD spectroscopy of the sulfoxide group in oxidized methionine and related compounds", Chemical Physics Letters, 2011, pp. 29-36, vol. 502.
Komori et al., "Structure Activity Relationships of Synthetic Antibiotic Analogues of Chryscandin", The Journal of Antibiotics, 1985, pp. 1182-1203, vol. 38, No. 9.
Li et al., "High Throughput Synthesis of Peptide α-Thioesters Through the Use of "Volatilizable" Support", Journal of Combinatorial Chemistry, 2008, pp. 613-616, vol. 10, No. 5 (and Supporting Information).
Roenne et al., "Lipase-Catalyzed Esterification of Lactic Acid with Straight-Chain Alcohols", J. American Oil Chemists' Society, 2005, pp. 881-885, vol. 82, No. 12.
Sato et al., "Oxidation of sulfides to sulfoxides and sulfones with 30% hydrogen peroxide under organic solvent- and halogen-free conditions", Tetrahedron, 2001, pp. 2469-2476, vol. 57.
Yoshiizumi et al., "Studies on Scavenger Receptor Inhibitors. Part 1: Synthesis and Structure—Activity Relationships of Novel Derivatives of Sulfatides", Bioorganic & Medicinal Chemistry, 2002, pp. 2445-2460, vol. 10.

(Continued)

*Primary Examiner* — Necholus Ogden, Jr.
(74) *Attorney, Agent, or Firm* — Polsinelli PC

(57) ABSTRACT

The present invention provides sulfoxide compounds comprising hydrophobic ester or amide moieties such that the compounds have surfactant properties. Also provided are methods for using the sulfoxide compounds or mixtures of the sulfoxide compounds in a variety of applications.

37 Claims, No Drawings

(56) References Cited

OTHER PUBLICATIONS

International Search Report and Written Opinion from related application, International Application No. PCT/US12/72016, dated Mar. 5, 2013, 9 pgs.
Third-Party Submission Under 37 CFR 1.290 from related U.S. Appl. No. 13/763,135 dated Apr. 10, 2014, 9 pgs.
Non-final Office action from related U.S. Appl. No. 13/763,101 dated Jun. 24, 2014, 10 pgs.
John, Synthesis and Modification of New Biodegradable Copolymers: Serine/Glycolic Acid Based Copolymers, New Biodegradable Copolymers, 1997, pp. 1901-1907.
Noga, Synthesis and Modification of Functional Poly(lactide) Copolymers: Towards Biofunctional Materials, biomacromolecules, 2008, 9, pp. 2056-2062.
Leemhuis, A versatile Route to Functionalized Dilactones as Monomers for the Synthesis of Poly(a-Hydroxy) Acids, Eur. J. Org. chem, 2003, pp. 3344-3349.

* cited by examiner

SULFOXIDE-BASED SURFACTANTS

CROSS-REFERENCE TO RELATED APPLICATIONS

This application claims the priority of U.S. provisional application No. 61/583,809, filed Jan. 6, 2012, which is hereby incorporated by reference in its entirety.

FIELD OF THE INVENTION

The present disclosure generally relates to surfactants. In particular, it relates to sulfoxide compounds comprising hydrophobic ester or amide moieties such that the compounds have surfactant properties.

BACKGROUND OF THE INVENTION

Surfactants (or surface active agents) are compounds that lower the surface tension of a liquid, the interfacial tension between two liquids, or the interfacial tension between a liquid and a solid. Surfactants function as cleaning, wetting, dispersing, emulsifying, foaming, and anti-foaming agents in numerous practical applications and products. Accordingly, surfactants are present in detergents and other cleaning products, cosmetics, and are used in a wide variety of industrial processes.

Because of the wide use of surfactants, there is a need for surfactants that are water soluble, tolerant to divalent cations, soluble over a wide range of concentrations and temperatures, rapidly biodegradable, and nontoxic.

SUMMARY OF THE INVENTION

Among the various aspects of the present disclosure is the provision of a compound comprising Formula (I):

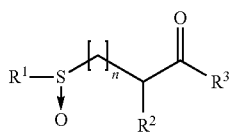

(I)

wherein:
- $R^1$ is hydrocarbyl or substituted hydrocarbyl;
- $R^2$ is OH, $OR^4$, $NH_2$, or $NHR^4$;
- $R^3$ is $OR^5$ or $NHR^5$;
- $R^4$ is hydrocarbyl or substituted hydrocarbyl;
- $R^5$ is hydrocarbyl or substituted hydrocarbyl having six or more carbon atoms in the principal chain; and
- n is an integer of 1 or greater;

provided, however, that when n is 1 and $R^2$ is $OR^4$, then $R^4$ comprises other than pyrrolyl or indolyl; when n is 2, $R^2$ is $NH_2$, and $R^3$ is $NHR^5$, then $R^5$ comprises other than aminoacyl, amide, piperidyl, pyridyl, pyrimidyl, or thioester; when n is 2 and $R^2$ is NH-methacryloyl, then $R^3$ is other than NH-menthyl; or when n is 2 and $R^3$ is NH—$C_{14}$ alkyl, then $R^2$ is other than $NH_2$ or NH—C(O)$(CH_2)_{16}CH_3$.

Another aspect of the present disclosure encompasses a compound comprising Formula (II):

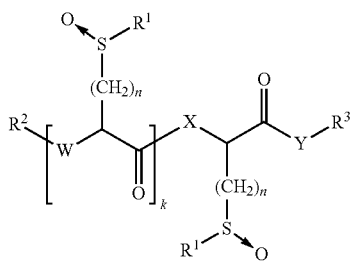

(II)

wherein:
- $R^1$ is hydrocarbyl or substituted hydrocarbyl;
- $R^2$ is hydrogen, hydrocarbyl, or substituted hydrocarbyl;
- $R^3$ is hydrocarbyl or substituted hydrocarbyl having six or more carbon atoms in the principal chain;
- W, X, and Y are independently O or NH; and
- k and n are independently integers of 1 or greater.

A further aspect of the present disclosure provides a composition comprising a mixture of compounds comprising Formula (II), the mixture comprising at least two different compounds comprising Formula (II):

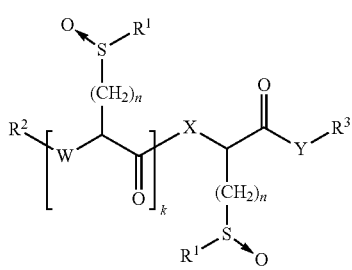

(II)

wherein:
- $R^1$ is hydrocarbyl or substituted hydrocarbyl;
- $R^2$ is hydrogen, hydrocarbyl, or substituted hydrocarbyl;
- $R^3$ is hydrocarbyl or substituted hydrocarbyl having six or more carbon atoms in the principal chain;
- W, X, and Y are independently O or NH;
- k is an integer of 0 or greater; and
- n is an integer of 1 or greater.

Still another aspect encompasses a process for cleaning an article, the process comprising contacting the article with a composition comprising at least one compound comprising Formula (II):

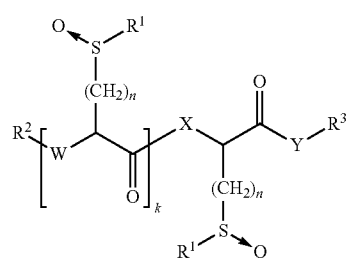

(II)

wherein:
R¹ is hydrocarbyl or substituted hydrocarbyl;
R² is H, hydrocarbyl, or substituted hydrocarbyl;
R³ is hydrocarbyl or substituted hydrocarbyl having six or more carbon atoms in the principal chain;
W, X, and Y are independently O or NH;
n is an integer of 1 or greater; and
k is an integer of 0 or greater.

Other features and iterations of the invention are described in more detail below.

DETAILED DESCRIPTION OF THE INVENTION

The present disclosure provides monomeric and oligomeric sulfoxide compounds comprising hydrophobic ester or amide moieties such that the compounds are interfacially active at both oil-water or air-water interfaces. Depending upon the selection of moieties, the sulfoxide compounds disclosed herein may be classified as water-soluble or oil-soluble. In particular, the water-soluble sulfoxide compounds have critical micelle concentrations in water, and water solutions containing the sulfoxide compounds have low surface tensions, and excellent tolerance to divalent cations (i.e., hardness tolerance). Additionally, the sulfoxide compounds disclosed herein are biodegradable and nontoxic. Consequently, the sulfoxide compounds disclosed herein are useful in many applications and products.

(I) Sulfoxide Compounds
    (a) Monomeric Compounds
One aspect of the invention provides compounds comprising Formula (I):

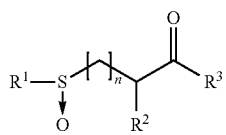

(I)

wherein:
R¹ is hydrocarbyl or substituted hydrocarbyl;
R² is OH, OR⁴, NH₂, or NHR⁴;
R³ is OR⁵ or NHR⁵;
R⁴ is hydrocarbyl or substituted hydrocarbyl;
R⁵ is hydrocarbyl or substituted hydrocarbyl having six or more carbon atoms in the principal chain; and
n is an integer of 1 or greater;
provided, however, that when n is 1 and R² is OR⁴, then R⁴ comprises other than a pyrrolyl or an indolyl group; when n is 2, R² is NH₂, and R³ is NHR⁵, then R⁵ comprises other than a aminoacyl, an amide, a piperidyl, a pyridyl, a pyrimidyl, or a thioester group; when n is 2 and R² is NH-methacryloyl, then R³ is other than NH-menthyl; or when n is 2 and R³ is NH—C₁₄ alkyl, then R² is other than NH₂ or NH—C(O)(CH₂)₁₆CH₃.

In some embodiments, R¹ may be alkyl, alkenyl, alkynyl, aryl, substituted alkyl, substituted alkenyl, substituted alkynyl, or substituted aryl. In exemplary embodiments, R¹ may be C₁ to C₁₀ alkyl, with the alkyl being linear or branched. For example, R¹ may be methyl, ethyl, propyl, butyl, etc. In exemplary embodiments, R¹ may be methyl.

In certain embodiments, R⁴ may be alkyl, alkenyl, alkynyl, aryl, substituted alkyl, substituted alkenyl, substituted alkynyl, or substituted aryl. For example, R⁴ may be acyl, acyloxy, alkyl, alkyoxy, aminoalkyl, thioalkyl, alkenyl, alkenyloxy, aryl, aryloxy, amine, amide, ester, or ether. In some embodiments, R⁴ may be methyl, ethyl, propyl, butyl, acetyl, propionyl, benzoyl, etc. In other embodiments, R⁴ may be $(CH_2CH_2O)_pH$, $(CH_2CH(CH_3)O)_pH$, or combinations thereof, wherein p is an integer of 2 or greater. In some embodiments, p may range from 2 to 20. In exemplary embodiments, p may range from 4 to 10.

In various embodiments, R⁵ may be alkyl, alkenyl, alkynyl, or aryl having six or more carbon atoms in the principal chain or R⁵ may be substituted alkyl, substituted alkenyl, substituted alkynyl, or substituted aryl having six or more carbon atoms in the principal chain. In some embodiments, R⁵ may be $C_6$ to $C_{30}$ alkyl, alkoxy, alkenyl, alkenyloxy, alkynyl, or alkynyloxy. In exemplary embodiments, R⁵ may be $C_6$ to $C_{22}$ alkyl (i.e., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl).

In one embodiment, n may be 2, R¹ may be methyl, R² may be NH₂, R³ may be OR⁵, and R⁵ may be $C_6$ to $C_{22}$ alkyl. In another embodiment, n may be 2; R¹ may be methyl, R² may be NH₂, R³ may be NHR⁵, and R⁵ may be $C_6$ to $C_{13}$ alkyl or $C_{15}$ to $C_{22}$ alkyl. In still another embodiment, n may be 2, R¹ may be methyl, R² may be NHR⁴, R⁴ may be $(CH_2CH_2O)_{2-20}H$, $(CH_2CH(CH_3)O)_{2-20}H$, or combinations thereof, R³ may be OR⁵ or NHR⁵, and R⁵ may be $C_6$ to $C_{22}$ alkyl.

In another embodiment, the compound comprising Formula (I) comprises Formula (Ia):

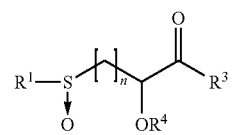

(Ia)

wherein:
R¹, R³, and n are as defined above for compounds comprising Formula (I); and
R⁴ is hydrogen, hydrocarbyl, or substituted hydrocarbyl;
provided, however, that when n is 1, then R⁴ comprises other than a pyrrolyl or an indolyl group.

In various embodiments, R⁴ may be hydrogen, acyl, acyloxy, alkyl, alkyoxy, aminoalkyl, thioalkyl, alkenyl, alkenyloxy, aryl, aryloxy, amine, amide, ester, or ether. For example, R⁴ may be $C_1$ to $C_{10}$ acyl, $C_1$ to $C_{10}$ alkyl, $(CH_2CH_2O)_{2-20}H$, $(CH_2CH(CH_3)O)_{2-20}H$, or a combination thereof. In some embodiments, R¹ may be $C_1$ to $C_{10}$ alkyl, R³ may be OR⁵ or NHR⁵, R⁴ may be hydrogen, $C_1$ to $C_{10}$ acyl, $(CH_2CH_2O)_{3-10}H$, $(CH_2CH(CH_3)O)_{3-10}H$, or a combination of $(CH_2CH_2O)_{3-10}H$ and $(CH_2CH(CH_3)O)_{3-10}H$, and R⁵ may be $C_6$ to $C_{30}$ alkyl. In one exemplary embodiment, n may be 2, R¹ may be methyl, R⁴ may be hydrogen, R³ may be OR⁵ or NHR⁵, and R⁵ may be $C_6$ to $C_{22}$ alkyl. In another exemplary embodiment, n may be 2, R¹ may be methyl, R⁴ may be $(CH_2CH_2O)_{2-20}H$, $(CH_2CH(CH_3)O)_{2-20}H$, or a combination thereof, R³ may be OR⁵ or NHR⁵, and R⁵ may be $C_6$ to $C_{22}$ alkyl. In still exemplary embodiment, n may be 2, R¹ may be methyl, R⁴ may be $C_1$ to $C_{10}$ acyl, R³ may be OR⁵ or NHR⁵, and R⁵ may be $C_6$ to $C_{22}$ alkyl.

In exemplary embodiments, n is 2. Exemplary ester compounds comprise Formula (Ib) and exemplary amide compounds comprise Formula (Ic), as diagrammed below:

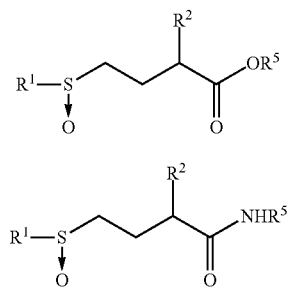

(Ib)

(Ic)

wherein;
R$^1$ is alkyl;
R$^2$ is OH, OR$^4$, NH$_2$, or NHR$^4$;
R$^4$ is C$_1$ to C$_{10}$ acyl, (CH$_2$CH$_2$O)$_{2-20}$H, (CH$_2$CH(CH$_3$)O)$_{2-20}$H, or a combination of (CH$_2$CH$_2$O)$_{2-20}$H and (CH$_2$CH(CH$_3$)O)$_{2-20}$H; and
R$^5$ is C$_6$ to C$_{22}$ alkyl;
provided that when R$^5$ in the compound comprising Formula (Ic) is C$_{14}$ alkyl, then R$^2$ is other than NH$_2$.

Table A presents exemplary compounds comprising Formula (I).

TABLE A

Exemplary compounds comprising Formula (I).

| # | R$^1$ | R$^2$ | R$^4$ | R$^3$ | R$^5$ |
|---|---|---|---|---|---|
| 1 | CH$_3$ | OH | — | OR$^5$ | C$_6$ alkyl |
| 2 | CH$_3$ | OH | — | OR$^5$ | C$_7$ alkyl |
| 3 | CH$_3$ | OH | — | OR$^5$ | C$_8$ alkyl |
| 4 | CH$_3$ | OH | — | OR$^5$ | C$_9$ alkyl |
| 5 | CH$_3$ | OH | — | OR$^5$ | C$_{10}$ alkyl |
| 6 | CH$_3$ | OH | — | OR$^5$ | C$_{11}$ alkyl |
| 7 | CH$_3$ | OH | — | OR$^5$ | C$_{12}$ alkyl |
| 8 | CH$_3$ | OH | — | OR$^5$ | C$_{14}$ alkyl |
|   | CH$_3$ | OH | — | OR$^5$ | C$_{15}$ alkyl |
| 9 | CH$_3$ | OH | — | OR$^5$ | C$_{16}$ alkyl |
| 10 | CH$_3$ | OH | — | OR$^5$ | C$_{17}$ alkyl |
| 11 | CH$_3$ | OH | — | OR$^5$ | C$_{18}$ alkyl |
| 12 | CH$_3$ | OH | — | OR$^5$ | C$_{19}$ alkyl |
| 13 | CH$_3$ | OH | — | OR$^5$ | C$_{20}$ alkyl |
| 14 | CH$_3$ | OH | — | OR$^5$ | C$_{21}$ alkyl |
| 15 | CH$_3$ | OH | — | OR$^5$ | C$_{22}$ alkyl |
| 16 | CH$_3$ | OH | — | NHR$^5$ | C$_6$ alkyl |
| 17 | CH$_3$ | OH | — | NHR$^5$ | C$_7$ alkyl |
| 18 | CH$_3$ | OH | — | NHR$^5$ | C$_8$ alkyl |
| 19 | CH$_3$ | OH | — | NHR$^5$ | C$_9$ alkyl |
| 20 | CH$_3$ | OH | — | NHR$^5$ | C$_{10}$ alkyl |
| 21 | CH$_3$ | OH | — | NHR$^5$ | C$_{11}$ alkyl |
| 22 | CH$_3$ | OH | — | NHR$^5$ | C$_{12}$ alkyl |
| 23 | CH$_3$ | OH | — | NHR$^5$ | C$_{13}$ alkyl |
| 24 | CH$_3$ | OH | — | NHR$^5$ | C$_{14}$ alkyl |
| 25 | CH$_3$ | OH | — | NHR$^5$ | C$_{15}$ alkyl |
| 26 | CH$_3$ | OH | — | NHR$^5$ | C$_{16}$ alkyl |
| 27 | CH$_3$ | OH | — | NHR$^5$ | C$_{17}$ alkyl |
| 28 | CH$_3$ | OH | — | NHR$^5$ | C$_{18}$ alkyl |
| 29 | CH$_3$ | OH | — | NHR$^5$ | C$_{19}$ alkyl |
| 30 | CH$_3$ | OH | — | NHR$^5$ | C$_{20}$ alkyl |
| 31 | CH$_3$ | OH | — | NHR$^5$ | C$_{21}$ alkyl |
| 32 | CH$_3$ | OH | — | NHR$^5$ | C$_{22}$ alkyl |
| 33 | CH$_3$ | OR$^4$ | acetyl | OR$^5$ | C$_6$ alkyl |
| 34 | CH$_3$ | OR$^4$ | acetyl | OR$^5$ | C$_7$ alkyl |
| 35 | CH$_3$ | OR$^4$ | acetyl | OR$^5$ | C$_8$ alkyl |
| 36 | CH$_3$ | OR$^4$ | acetyl | OR$^5$ | C$_9$ alkyl |
| 37 | CH$_3$ | OR$^4$ | acetyl | OR$^5$ | C$_{10}$ alkyl |
| 38 | CH$_3$ | OR$^4$ | acetyl | OR$^5$ | C$_{11}$ alkyl |
| 39 | CH$_3$ | OR$^4$ | acetyl | OR$^5$ | C$_{12}$ alkyl |
| 40 | CH$_3$ | OR$^4$ | acetyl | OR$^5$ | C$_{13}$ alkyl |
| 41 | CH$_3$ | OR$^4$ | acetyl | OR$^5$ | C$_{14}$ alkyl |
| 42 | CH$_3$ | OR$^4$ | acetyl | OR$^5$ | C$_{15}$ alkyl |
| 43 | CH$_3$ | OR$^4$ | acetyl | OR$^5$ | C$_{16}$ alkyl |
| 44 | CH$_3$ | OR$^4$ | acetyl | OR$^5$ | C$_{17}$ alkyl |
| 45 | CH$_3$ | OR$^4$ | acetyl | OR$^5$ | C$_{18}$ alkyl |
| 46 | CH$_3$ | OR$^4$ | acetyl | OR$^5$ | C$_{19}$ alkyl |
| 47 | CH$_3$ | OR$^4$ | acetyl | OR$^5$ | C$_{20}$ alkyl |
| 48 | CH$_3$ | OR$^4$ | acetyl | OR$^5$ | C$_{21}$ alkyl |
| 49 | CH$_3$ | OR$^4$ | acetyl | OR$^5$ | C$_{22}$ alkyl |
| 50 | CH$_3$ | OR$^4$ | acetyl | NHR$^5$ | C$_6$ alkyl |
| 51 | CH$_3$ | OR$^4$ | acetyl | NHR$^5$ | C$_7$ alkyl |
| 52 | CH$_3$ | OR$^4$ | acetyl | NHR$^5$ | C$_8$ alkyl |
| 53 | CH$_3$ | OR$^4$ | acetyl | NHR$^5$ | C$_9$ alkyl |
| 54 | CH$_3$ | OR$^4$ | acetyl | NHR$^5$ | C$_{10}$ alkyl |
| 55 | CH$_3$ | OR$^4$ | acetyl | NHR$^5$ | C$_{11}$ alkyl |
| 56 | CH$_3$ | OR$^4$ | acetyl | NHR$^5$ | C$_{12}$ alkyl |
| 57 | CH$_3$ | OR$^4$ | acetyl | NHR$^5$ | C$_{13}$ alkyl |
| 58 | CH$_3$ | OR$^4$ | acetyl | NHR$^5$ | C$_{14}$ alkyl |
| 59 | CH$_3$ | OR$^4$ | acetyl | NHR$^5$ | C$_{15}$ alkyl |
| 60 | CH$_3$ | OR$^4$ | acetyl | NHR$^5$ | C$_{16}$ alkyl |
| 61 | CH$_3$ | OR$^4$ | acetyl | NHR$^5$ | C$_{17}$ alkyl |
| 62 | CH$_3$ | OR$^4$ | acetyl | NHR$^5$ | C$_{18}$ alkyl |
| 63 | CH$_3$ | OR$^4$ | acetyl | NHR$^5$ | C$_{19}$ alkyl |
| 64 | CH$_3$ | OR$^4$ | acetyl | NHR$^5$ | C$_{20}$ alkyl |
| 65 | CH$_3$ | OR$^4$ | acetyl | NHR$^5$ | C$_{21}$ alkyl |
| 66 | CH$_3$ | OR$^4$ | acetyl | NHR$^5$ | C$_{22}$ alkyl |
| 67 | CH$_3$ | OR$^4$ | (CH$_2$CH$_2$O)$_{4-10}$H | OR$^5$ | C$_6$ alkyl |
| 68 | CH$_3$ | OR$^4$ | (CH$_2$CH$_2$O)$_{4-10}$H | OR$^5$ | C$_7$ alkyl |
| 69 | CH$_3$ | OR$^4$ | (CH$_2$CH$_2$O)$_{4-10}$H | OR$^5$ | C$_8$ alkyl |
| 70 | CH$_3$ | OR$^4$ | (CH$_2$CH$_2$O)$_{4-10}$H | OR$^5$ | C$_9$ alkyl |
| 71 | CH$_3$ | OR$^4$ | (CH$_2$CH$_2$O)$_{4-10}$H | OR$^5$ | C$_{10}$ alkyl |
| 72 | CH$_3$ | OR$^4$ | (CH$_2$CH$_2$O)$_{4-10}$H | OR$^5$ | C$_{11}$ alkyl |
| 73 | CH$_3$ | OR$^4$ | (CH$_2$CH$_2$O)$_{4-10}$H | OR$^5$ | C$_{12}$ alkyl |
| 74 | CH$_3$ | OR$^4$ | (CH$_2$CH$_2$O)$_{4-10}$H | OR$^5$ | C$_{13}$ alkyl |
| 75 | CH$_3$ | OR$^4$ | (CH$_2$CH$_2$O)$_{4-10}$H | OR$^5$ | C$_{14}$ alkyl |
| 76 | CH$_3$ | OR$^4$ | (CH$_2$CH$_2$O)$_{4-10}$H | OR$^5$ | C$_{15}$ alkyl |
| 77 | CH$_3$ | OR$^4$ | (CH$_2$CH$_2$O)$_{4-10}$H | OR$^5$ | C$_{16}$ alkyl |
| 78 | CH$_3$ | OR$^4$ | (CH$_2$CH$_2$O)$_{4-10}$H | OR$^5$ | C$_{17}$ alkyl |
| 79 | CH$_3$ | OR$^4$ | (CH$_2$CH$_2$O)$_{4-10}$H | OR$^5$ | C$_{18}$ alkyl |
| 80 | CH$_3$ | OR$^4$ | (CH$_2$CH$_2$O)$_{4-10}$H | OR$^5$ | C$_{19}$ alkyl |
| 81 | CH$_3$ | OR$^4$ | (CH$_2$CH$_2$O)$_{4-10}$H | OR$^5$ | C$_{20}$ alkyl |
| 82 | CH$_3$ | OR$^4$ | (CH$_2$CH$_2$O)$_{4-10}$H | OR$^5$ | C$_{21}$ alkyl |
| 83 | CH$_3$ | OR$^4$ | (CH$_2$CH$_2$O)$_{4-10}$H | OR$^5$ | C$_{22}$ alkyl |
| 84 | CH$_3$ | OR$^4$ | (CH$_2$CH$_2$O)$_{4-10}$H | NHR$^5$ | C$_6$ alkyl |
| 85 | CH$_3$ | OR$^4$ | (CH$_2$CH$_2$O)$_{4-10}$H | NHR$^5$ | C$_7$ alkyl |
| 86 | CH$_3$ | OR$^4$ | (CH$_2$CH$_2$O)$_{4-10}$H | NHR$^5$ | C$_8$ alkyl |
| 87 | CH$_3$ | OR$^4$ | (CH$_2$CH$_2$O)$_{4-10}$H | NHR$^5$ | C$_9$ alkyl |
| 88 | CH$_3$ | OR$^4$ | (CH$_2$CH$_2$O)$_{4-10}$H | NHR$^5$ | C$_{10}$ alkyl |
| 89 | CH$_3$ | OR$^4$ | (CH$_2$CH$_2$O)$_{4-10}$H | NHR$^5$ | C$_{11}$ alkyl |
| 90 | CH$_3$ | OR$^4$ | (CH$_2$CH$_2$O)$_{4-10}$H | NHR$^5$ | C$_{12}$ alkyl |
| 91 | CH$_3$ | OR$^4$ | (CH$_2$CH$_2$O)$_{4-10}$H | NHR$^5$ | C$_{13}$ alkyl |
| 92 | CH$_3$ | OR$^4$ | (CH$_2$CH$_2$O)$_{4-10}$H | NHR$^5$ | C$_{14}$ alkyl |
| 93 | CH$_3$ | OR$^4$ | (CH$_2$CH$_2$O)$_{4-10}$H | NHR$^5$ | C$_{15}$ alkyl |
| 94 | CH$_3$ | OR$^4$ | (CH$_2$CH$_2$O)$_{4-10}$H | NHR$^5$ | C$_{16}$ alkyl |
| 95 | CH$_3$ | OR$^4$ | (CH$_2$CH$_2$O)$_{4-10}$H | NHR$^5$ | C$_{17}$ alkyl |
| 96 | CH$_3$ | OR$^4$ | (CH$_2$CH$_2$O)$_{4-10}$H | NHR$^5$ | C$_{18}$ alkyl |
| 97 | CH$_3$ | OR$^4$ | (CH$_2$CH$_2$O)$_{4-10}$H | NHR$^5$ | C$_{19}$ alkyl |
| 98 | CH$_3$ | OR$^4$ | (CH$_2$CH$_2$O)$_{4-10}$H | NHR$^5$ | C$_{20}$ alkyl |
| 99 | CH$_3$ | OR$^4$ | (CH$_2$CH$_2$O)$_{4-10}$H | NHR$^5$ | C$_{21}$ alkyl |
| 100 | CH$_3$ | OR$^4$ | (CH$_2$CH$_2$O)$_{4-10}$H | NHR$^5$ | C$_{22}$ alkyl |
| 101 | CH$_3$ | NH$_2$ | — | OR$^5$ | C$_6$ alkyl |
| 102 | CH$_3$ | NH$_2$ | — | OR$^5$ | C$_7$ alkyl |
| 103 | CH$_3$ | NH$_2$ | — | OR$^5$ | C$_8$ alkyl |
| 104 | CH$_3$ | NH$_2$ | — | OR$^5$ | C$_9$ alkyl |
| 105 | CH$_3$ | NH$_2$ | — | OR$^5$ | C$_{10}$ alkyl |
| 106 | CH$_3$ | NH$_2$ | — | OR$^5$ | C$_{11}$ alkyl |
| 107 | CH$_3$ | NH$_2$ | — | OR$^5$ | C$_{12}$ alkyl |
| 108 | CH$_3$ | NH$_2$ | — | OR$^5$ | C$_{13}$ alkyl |
| 109 | CH$_3$ | NH$_2$ | — | OR$^5$ | C$_{14}$ alkyl |
| 110 | CH$_3$ | NH$_2$ | — | OR$^5$ | C$_{15}$ alkyl |
| 111 | CH$_3$ | NH$_2$ | — | OR$^5$ | C$_{16}$ alkyl |
| 112 | CH$_3$ | NH$_2$ | — | OR$^5$ | C$_{17}$ alkyl |
| 113 | CH$_3$ | NH$_2$ | — | OR$^5$ | C$_{18}$ alkyl |
| 114 | CH$_3$ | NH$_2$ | — | OR$^5$ | C$_{19}$ alkyl |
| 115 | CH$_3$ | NH$_2$ | — | OR$^5$ | C$_{20}$ alkyl |
| 116 | CH$_3$ | NH$_2$ | — | OR$^5$ | C$_{21}$ alkyl |
| 117 | CH$_3$ | NH$_2$ | — | OR$^5$ | C$_{22}$ alkyl |
| 118 | CH$_3$ | NH$_2$ | — | NHR$^5$ | C$_6$ alkyl |

TABLE A-continued

Exemplary compounds comprising Formula (I).

| # | $R^1$ | $R^2$ | $R^4$ | $R^3$ | $R^5$ |
|---|---|---|---|---|---|
| 119 | $CH_3$ | $NH_2$ | — | $NHR^5$ | $C_7$ alkyl |
| 120 | $CH_3$ | $NH_2$ | — | $NHR^5$ | $C_8$ alkyl |
| 121 | $CH_3$ | $NH_2$ | — | $NHR^5$ | $C_9$ alkyl |
| 123 | $CH_3$ | $NH_2$ | — | $NHR^5$ | $C_{10}$ alkyl |
| 124 | $CH_3$ | $NH_2$ | — | $NHR^5$ | $C_{11}$ alkyl |
| 125 | $CH_3$ | $NH_2$ | — | $NHR^5$ | $C_{12}$ alkyl |
| 126 | $CH_3$ | $NH_2$ | — | $NHR^5$ | $C_{14}$ alkyl |
| 127 | $CH_3$ | $NH_2$ | — | $NHR^5$ | $C_{15}$ alkyl |
| 128 | $CH_3$ | $NH_2$ | — | $NHR^5$ | $C_{16}$ alkyl |
| 129 | $CH_3$ | $NH_2$ | — | $NHR^5$ | $C_{187}$ alkyl |
| 130 | $CH_3$ | $NH_2$ | — | $NHR^5$ | $C_{18}$ alkyl |
| 131 | $CH_3$ | $NH_2$ | — | $NHR^5$ | $C_{19}$ alkyl |
| 132 | $CH_3$ | $NH_2$ | — | $NHR^5$ | $C_{20}$ alkyl |
| 133 | $CH_3$ | $NH_2$ | — | $NHR^5$ | $C_{21}$ alkyl |
| 134 | $CH_3$ | $NH_2$ | — | $NHR^5$ | $C_{22}$ alkyl |

In exemplary compounds comprising Formula (I), n is 2, $R^1$ is methyl, $R^2$ is OH, $NH_2$, $O(CH_2CH_2O)_{4-10}H$, or $NH(CH_2CH_2O)_{4-10}H$; and $R^3$ is O—$C_{6-22}$ alkyl or NH—$C_{6-22}$ alkyl, provided however that when $R^2$ is $NH_2$, then $R^3$ is other than NH $C_{14}$ alkyl. Structures of such exemplary compounds are presented below:

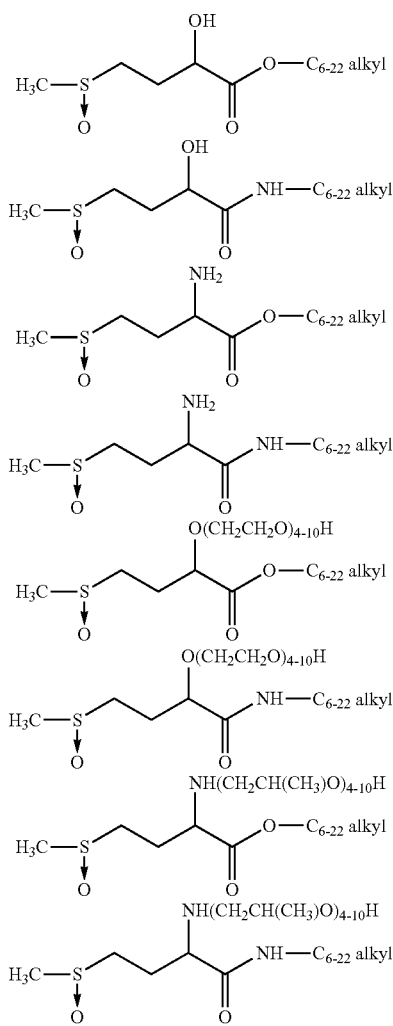

(b) Oligomeric Compounds

A further aspect of the disclosure provides compounds comprising Formula (II):

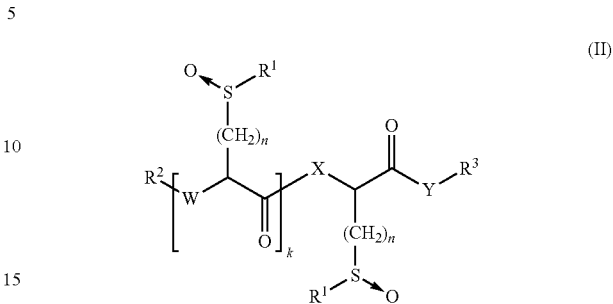

wherein:

$R^1$ is hydrocarbyl or substituted hydrocarbyl;

$R^2$ is hydrogen, hydrocarbyl, or substituted hydrocarbyl;

$R^3$ is hydrocarbyl or substituted hydrocarbyl having six or more carbon atoms in the principal chain;

W, X, and Y are independently O or NH; and k and n are independently integers of 1 or greater In various embodiments, $R^1$ may be alkyl, alkenyl, alkynyl, aryl, substituted alkyl, substituted alkenyl, substituted alkynyl, or substituted aryl. In certain embodiments, $R^1$ may be $C_1$ to $C_{10}$ alkyl. In exemplary embodiments, $R^1$ may be methyl.

In some embodiments, $R^2$ may be hydrogen, alkyl, alkenyl, alkynyl, aryl, substituted alkyl, substituted alkenyl, substituted alkynyl, or substituted aryl. For example, $R^2$ may be acyl, acyloxy, alkyl, alkyoxy, aminoalkyl, thioalkyl, alkenyl, alkenyloxy, aryl, aryloxy, amine, amide, ester, or ether. In some embodiments, $R^2$ may be hydrogen. In other embodiments, $R^2$ may be methyl, ethyl, propyl, butyl, acetyl, propionyl, benzoyl, etc. In still other embodiments, $R^2$ may be $(CH_2CH_2O)_pH$, $(CH_2CH(CH_3)O)_pH$, or combinations thereof, wherein p is an integer of 2 or greater. In some embodiments, p may range from 2 to 20, or p may range from 4 to 10.

In certain embodiments, $R^3$ may be alkyl, alkenyl, alkynyl, or aryl having six or more carbon atoms in the principal chain or $R^3$ may be substituted alkyl, substituted alkenyl, substituted alkynyl, or substituted aryl having six or more carbon atoms in the principal chain. In some embodiments, $R^3$ may be $C_6$ to $0_{30}$ alkyl, alkoxy, alkenyl, alkenyloxy, alkynyl, or alkynyloxy. In exemplary embodiments, $R^3$ may be $C_6$ to $C_{22}$ alkyl (i.e., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl).

In exemplary embodiments, $R^1$ may be $C_1$ to $C_{10}$ alkyl, $R^2$ may be hydrogen, acyl, $(CH_2CH_2O)_{2-20}H$, $(CH_2CH(CH_3)O)_{2-20}H$, or a combination of $(CH_2CH_2O)_{2-20}H$ and $(CH_2CH(CH_3)O)_{2-20}H$, and $R^3$ may be $C_6$ to $C_{30}$ alkyl. In certain iterations, W, X, and Y may be oxygen. In other iterations, W and X may be oxygen and Y may be NH. In various embodiments, k may be 1, 2, 3, or more, such that the compound is a dimer, trimer, tetramer, or higher order oligomer, respectively.

In one embodiment, n is 2 and the compound comprising Formula (II) comprises Formula (IIa):

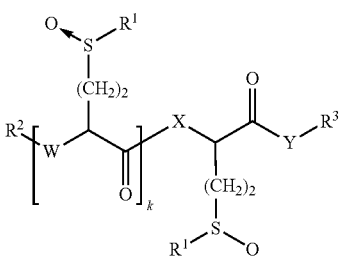

(IIa)

wherein, $R^1$, $R^2$, $R^3$, W, X, Y, and k are as defined above for compounds comprising Formula (II).

In some iterations of compounds comprising Formula (IIa) in which n is 2, $R^1$ may be methyl, $R^2$ may be hydrogen, Y may be NH or O, and $R^3$ may be $C_6$ to $C_{22}$ alkyl. Shown below are such compounds in which k is 1 (i.e., dimer), k is 2 (i.e., trimer), or k is 3 (i.e., tetramer).

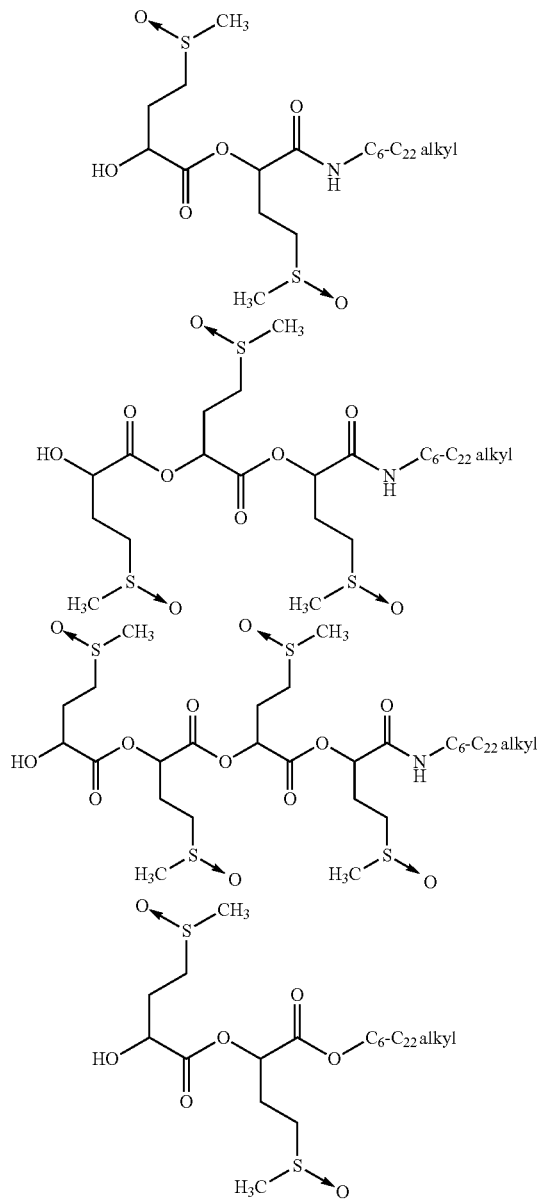

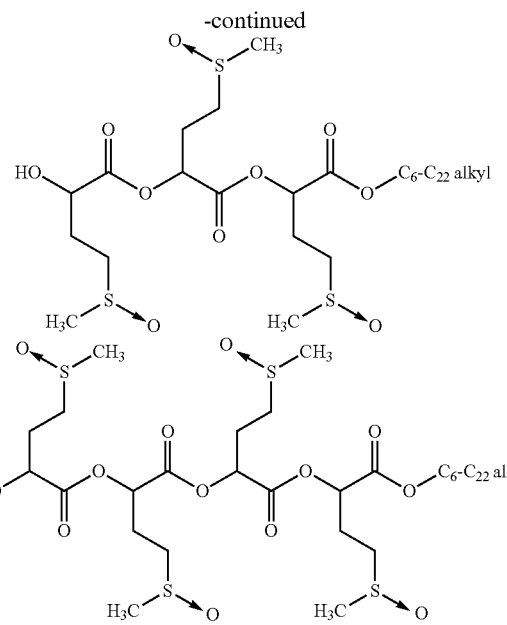

(c) Stereochemistry

In general, the compounds disclosed herein have chiral centers. For example, in monomer compounds, the alpha carbon adjacent to the carbonyl unit is chiral. In dimer, trimer, and higher order oligomer compounds, each alpha carbon adjacent to a carbonyl unit is chiral. The sulfur of the sulfoxide group is also chiral. Shown below are specific monomer, dimer, or trimer compounds in which each chiral center is denoted with an asterisk.

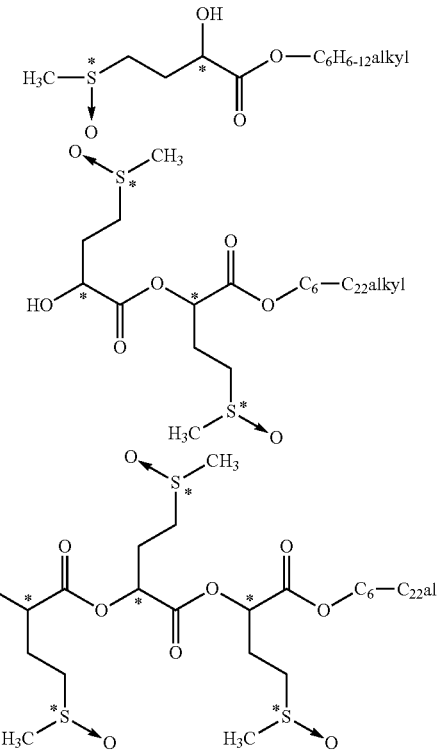

Each chiral center may have an R or an S configuration. For example, the configuration of the chiral carbon and sulfur atoms in a monomer compound may be RR, RS, SR, or SS, respectively. In dimer compounds, the configuration of the two chiral carbon atoms and two chiral sulfur atoms may be RRRR, RRRS, RRSR, RRSS, RSRS, RSRR, RSSR, RSSS, SRRR, SRRS, SRSR, SRSS, SSRS, SSRR, SSSR, and SSSS, respectively. In trimer and higher order oligo compounds, the configuration of the chiral centers may vary in a similar manner. Moreover, the compounds comprising Formulas (I) or (II) may have additional chiral center, depending on the identity of the various R groups. Each additional chiral may be independently R or S.

(d) Properties

In general, if the compound comprising Formulas (I) or (II) detailed above has sufficient water solubility, then it has a critical micelle concentration (CMC) in water at 25° C. and atmospheric pressure. For example, the CMC of compounds comprising Formulas (I) or (II) may range from about 0.0001 to about 100 mM in water at 25° C. and atmospheric pressure. In various embodiments, the compounds comprising Formulas (I) or (II) may have a CMC that ranges from about 0.0001 to about 0.0003, from about 0.0003 to about 0.001, from about 0.001 to about 0.003, from about 0.003 to about 0.01, from about 0.01 to about 0.03, from about 0.03 to about 0.1, from about 0.1 to about 0.3, from about 0.3 to about 1, from about 1 to about 3, from about 3 to about 10, from about 10 to about 30, or from about 30 to about 100 mM in water at 25° C. and atmospheric pressure. In various embodiments, the compounds comprising Formulas (I) or (II) may have a CMC of less than about 0.3 mM, less than about 0.1 mM, less than about 0.03 mM, less than about 0.01 mM, less than about 0.003 mM, or less than about 0.001 mM in water at 25° C. and atmospheric pressure.

Additionally, if the compound comprising Formulas (I) or (II) has sufficient water solubility, then it reduces the surface tension of water significantly. Thus, the compounds comprising Formulas (I) or (II) when added to water may cause the surface tension of water to range from about 15 mN/m to about 50 mN/m at CMC (at 25° C. and atmospheric pressure). In certain embodiments, the compounds comprising Formulas (I) or (II) when added to water may reduce the surface tension of water to about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mN/m at CMC (at 25° C. and atmospheric pressure).

(II) Compositions (a) Mixture of Compounds

Another aspect of the present disclosure encompasses a composition comprising a mixture of compounds comprising Formula (II), the mixture comprising at least two different compounds comprising Formula (II):

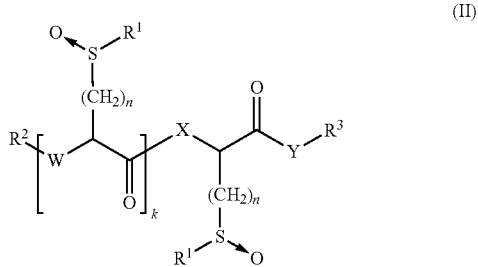

wherein:
$R^1$, $R^2$, $R^3$, W, X, Y, and n are as defined above for the compound comprising Formula (II): and
k is an integer of 0 or greater.

In certain embodiments, $R^1$ may be $C_1$ to $C_{10}$ alkyl, $R^2$ may be hydrogen, acyl, $(CH_2CH_2O)_{2-20}H$, $(CH_2CH(CH_3)O)_{2-20}H$, or a combination of $(CH_2CH_2O)_{2-20}H$ and $(CH_2CH(CH_3)O)_{2-20}H$, and $R^3$ may be $C_6$ to $C_{30}$ alkyl. In exemplary embodiments, n may be 2, $R^1$ may be methyl, $R^2$ may be hydrogen, $R^3$ may be $C_6$ to $C_{22}$ alkyl, and W and X may be oxygen.

In some embodiments, the composition may comprise compounds in which k is constant and at least one of $R^1$, $R^2$, $R^3$, W, X, Y, or n varies. For example, the composition may comprise a mixture of 2, 3, 4, or more different monomers in which $R^3$ varies; a mixture of 2, 3, 4, or more different dimers in which $R^3$ varies; a mixture of 2, 3, 4 or more different timers in which $R^3$ varies, a mixture of 2, 3, 4, or more different tetramers in which $R^3$ varies, and so forth. For example, the mixture may comprise a first set of compounds in which k is 0 and $R^3$ is $C_{6-22}$ alkyl and a second set of compounds in which k is 0 and $R^3$ is $C_{6-22}$ alkyl, provided that $R^3$ differs in each of the two sets. Alternatively, the mixture may comprise a first set of compounds in which k is 0 and $R^3$ is $C_{6-22}$ alkyl, a second set of compounds in which k is 0 and $R^3$ is $C_{6-22}$ alkyl, and a third set of compounds in k is 0 and $R^3$ is $C_{6-22}$ alkyl, provided that $R^3$ differs in each of the three sets. In another embodiment, the mixture may comprise a first set of compounds in which k is 1 and $R^3$ is $C_{6-22}$ alkyl and a second set of compounds in which k is 1 and $R^3$ is $C_{6-22}$ alkyl, provided that $R^3$ differs in each of the two sets. In yet another embodiment, the mixture may comprise a first set of compounds in which k is 2 and $R^3$ is $C_{6-22}$ alkyl and a second set of compounds in which k is 2 and $R^3$ is $C_{6-22}$ alkyl, provided that $R^3$ differs in each of the two sets. Numerous other combinations are encompassed by the invention.

In other embodiments, the composition may comprise compounds in which k varies and each of $R^1$, $R^2$, $R^3$, W, X, Y, and n is the same. Thus, the composition may comprise a mixture of monomers and dimers in which all the substituents/variables are identical in all the compounds; a mixture of monomers, dimers, and trimers in which all the substituents/variables are identical in all the compounds; or a mixture of monomers and oligomers in which all the substituents/variables are identical in all the compounds; etc. For example, the mixture may comprise a first set of compounds in which k is 0 and a second set of compounds in which k is 1, wherein each of $R^1$, $R^2$, $R^3$, W, X, Y, and n is identical in the two sets. In another example, the mixture may comprise a first set of compounds in which k is 0, a second set of compounds in which k is 1, and a third set of compounds in which k is 2, wherein each of $R^1$, $R^2$, $R^3$, W, X, Y, and n is identical in each set. In still another example, the mixture may comprise a first set of compounds in which k is 0, a second set of compounds in which k is 1, a third set of compounds in which k is 2, and a fourth set of compounds in which k is 3, wherein each of $R^1$, $R^2$, $R^3$, W, X, Y, and n is identical in each set of compounds.

In still further embodiments, the composition may comprise compounds in which each of $R^1$, $R^2$, $R^3$, W, X, Y, k and n varies.

Table B presents a non-exhaustive list of possible mixtures of compounds comprising two or three different sets of compounds in which k or $R^3$ varies.

TABLE B

Mixtures of Compounds Comprising Two or Three Sets of Compounds

| First set of compounds | | Second set of compounds | | Third set of compounds | |
|---|---|---|---|---|---|
| k | $R^3$ | k | $R^3$ | k | $R^3$ |
| 0 | $C_6$ alkyl | 0 | $C_7$ alkyl | — | — |
| 0 | $C_6$ alkyl | 0 | $C_8$ alkyl | — | — |
| 0 | $C_6$ alkyl | 0 | $C_9$ alkyl | — | — |
| 0 | $C_6$ alkyl | 0 | $C_{10}$ alkyl | — | — |
| 0 | $C_6$ alkyl | 0 | $C_{11}$ alkyl | — | — |
| 0 | $C_6$ alkyl | 0 | $C_{12}$ alkyl | — | — |
| 0 | $C_6$ alkyl | 0 | $C_{13}$ alkyl | — | — |
| 0 | $C_6$ alkyl | 0 | $C_{14}$ alkyl | — | — |
| 0 | $C_6$ alkyl | 0 | $C_{15}$ alkyl | — | — |
| 0 | $C_6$ alkyl | 0 | $C_{16}$ alkyl | — | — |
| 0 | $C_6$ alkyl | 0 | $C_{17}$ alkyl | — | — |
| 0 | $C_6$ alkyl | 0 | $C_{18}$ alkyl | — | — |
| 0 | $C_6$ alkyl | 0 | $C_{19}$ alkyl | — | — |
| 0 | $C_6$ alkyl | 0 | $C_{20}$ alkyl | — | — |
| 0 | $C_6$ alkyl | 0 | $C_{21}$ alkyl | — | — |
| 0 | $C_6$ alkyl | 0 | $C_{22}$ alkyl | — | — |
| 0 | $C_7$ alkyl | 0 | $C_8$ alkyl | — | — |
| 0 | $C_7$ alkyl | 0 | $C_9$ alkyl | — | — |
| 0 | $C_7$ alkyl | 0 | $C_{10}$ alkyl | — | — |
| 0 | $C_7$ alkyl | 0 | $C_{11}$ alkyl | — | — |
| 0 | $C_7$ alkyl | 0 | $C_{12}$ alkyl | — | — |
| 0 | $C_7$ alkyl | 0 | $C_{13}$ alkyl | — | — |
| 0 | $C_7$ alkyl | 0 | $C_{14}$ alkyl | — | — |
| 0 | $C_7$ alkyl | 0 | $C_{15}$ alkyl | — | — |
| 0 | $C_7$ alkyl | 0 | $C_{16}$ alkyl | — | — |
| 0 | $C_7$ alkyl | 0 | $C_{17}$ alkyl | — | — |
| 0 | $C_7$ alkyl | 0 | $C_{18}$ alkyl | — | — |
| 0 | $C_7$ alkyl | 0 | $C_{19}$ alkyl | — | — |
| 0 | $C_7$ alkyl | 0 | $C_{20}$ alkyl | — | — |
| 0 | $C_7$ alkyl | 0 | $C_{21}$ alkyl | — | — |
| 0 | $C_7$ alkyl | 0 | $C_{22}$ alkyl | — | — |
| 0 | $C_8$ alkyl | 0 | $C_9$ alkyl | — | — |
| 0 | $C_8$ alkyl | 0 | $C_{10}$ alkyl | — | — |
| 0 | $C_8$ alkyl | 0 | $C_{11}$ alkyl | — | — |
| 0 | $C_8$ alkyl | 0 | $C_{12}$ alkyl | — | — |
| 0 | $C_8$ alkyl | 0 | $C_{13}$ alkyl | — | — |
| 0 | $C_8$ alkyl | 0 | $C_{14}$ alkyl | — | — |
| 0 | $C_8$ alkyl | 0 | $C_{15}$ alkyl | — | — |
| 0 | $C_8$ alkyl | 0 | $C_{16}$ alkyl | — | — |
| 0 | $C_8$ alkyl | 0 | $C_{17}$ alkyl | — | — |
| 0 | $C_8$ alkyl | 0 | $C_{18}$ alkyl | — | — |
| 0 | $C_8$ alkyl | 0 | $C_{19}$ alkyl | — | — |
| 0 | $C_8$ alkyl | 0 | $C_{20}$ alkyl | — | — |
| 0 | $C_8$ alkyl | 0 | $C_{21}$ alkyl | — | — |
| 0 | $C_8$ alkyl | 0 | $C_{22}$ alkyl | — | — |
| 0 | $C_9$ alkyl | 0 | $C_{10}$ alkyl | — | — |
| 0 | $C_9$ alkyl | 0 | $C_{11}$ alkyl | — | — |
| 0 | $C_9$ alkyl | 0 | $C_{12}$ alkyl | — | — |
| 0 | $C_9$ alkyl | 0 | $C_{13}$ alkyl | — | — |
| 0 | $C_9$ alkyl | 0 | $C_{14}$ alkyl | — | — |
| 0 | $C_9$ alkyl | 0 | $C_{15}$ alkyl | — | — |
| 0 | $C_9$ alkyl | 0 | $C_{16}$ alkyl | — | — |
| 0 | $C_9$ alkyl | 0 | $C_{17}$ alkyl | — | — |
| 0 | $C_9$ alkyl | 0 | $C_{18}$ alkyl | — | — |
| 0 | $C_9$ alkyl | 0 | $C_{19}$ alkyl | — | — |
| 0 | $C_9$ alkyl | 0 | $C_{20}$ alkyl | — | — |
| 0 | $C_9$ alkyl | 0 | $C_{21}$ alkyl | — | — |
| 0 | $C_9$ alkyl | 0 | $C_{22}$ alkyl | — | — |
| 0 | $C_{10}$ alkyl | 0 | $C_{11}$ alkyl | — | — |
| 0 | $C_{10}$ alkyl | 0 | $C_{12}$ alkyl | — | — |
| 0 | $C_{10}$ alkyl | 0 | $C_{13}$ alkyl | — | — |
| 0 | $C_{10}$ alkyl | 0 | $C_{14}$ alkyl | — | — |
| 0 | $C_{10}$ alkyl | 0 | $C_{15}$ alkyl | — | — |
| 0 | $C_{10}$ alkyl | 0 | $C_{16}$ alkyl | — | — |
| 0 | $C_{10}$ alkyl | 0 | $C_{17}$ alkyl | — | — |
| 0 | $C_{10}$ alkyl | 0 | $C_{18}$ alkyl | — | — |
| 0 | $C_{10}$ alkyl | 0 | $C_{19}$ alkyl | — | — |
| 0 | $C_{10}$ alkyl | 0 | $C_{20}$ alkyl | — | — |
| 0 | $C_{10}$ alkyl | 0 | $C_{21}$ alkyl | — | — |
| 0 | $C_{10}$ alkyl | 0 | $C_{22}$ alkyl | — | — |
| 0 | $C_{11}$ alkyl | 0 | $C_{12}$ alkyl | — | — |
| 0 | $C_{11}$ alkyl | 0 | $C_{13}$ alkyl | — | — |
| 0 | $C_{11}$ alkyl | 0 | $C_{14}$ alkyl | — | — |
| 0 | $C_{11}$ alkyl | 0 | $C_{15}$ alkyl | — | — |
| 0 | $C_{11}$ alkyl | 0 | $C_{16}$ alkyl | — | — |
| 0 | $C_{11}$ alkyl | 0 | $C_{17}$ alkyl | — | — |
| 0 | $C_{11}$ alkyl | 0 | $C_{18}$ alkyl | — | — |
| 0 | $C_{11}$ alkyl | 0 | $C_{19}$ alkyl | — | — |
| 0 | $C_{11}$ alkyl | 0 | $C_{20}$ alkyl | — | — |
| 0 | $C_{11}$ alkyl | 0 | $C_{21}$ alkyl | — | — |
| 0 | $C_{11}$ alkyl | 0 | $C_{22}$ alkyl | — | — |
| 0 | $C_{12}$ alkyl | 0 | $C_{13}$ alkyl | — | — |
| 0 | $C_{12}$ alkyl | 0 | $C_{14}$ alkyl | — | — |
| 0 | $C_{12}$ alkyl | 0 | $C_{15}$ alkyl | — | — |
| 0 | $C_{12}$ alkyl | 0 | $C_{16}$ alkyl | — | — |
| 0 | $C_{12}$ alkyl | 0 | $C_{17}$ alkyl | — | — |
| 0 | $C_{12}$ alkyl | 0 | $C_{18}$ alkyl | — | — |
| 0 | $C_{12}$ alkyl | 0 | $C_{19}$ alkyl | — | — |
| 0 | $C_{12}$ alkyl | 0 | $C_{20}$ alkyl | — | — |
| 0 | $C_{12}$ alkyl | 0 | $C_{21}$ alkyl | — | — |
| 0 | $C_{12}$ alkyl | 0 | $C_{22}$ alkyl | — | — |
| 0 | $C_{13}$ alkyl | 0 | $C_{14}$ alkyl | — | — |
| 0 | $C_{13}$ alkyl | 0 | $C_{15}$ alkyl | — | — |
| 0 | $C_{13}$ alkyl | 0 | $C_{16}$ alkyl | — | — |
| 0 | $C_{13}$ alkyl | 0 | $C_{17}$ alkyl | — | — |
| 0 | $C_{13}$ alkyl | 0 | $C_{18}$ alkyl | — | — |
| 0 | $C_{13}$ alkyl | 0 | $C_{19}$ alkyl | — | — |
| 0 | $C_{13}$ alkyl | 0 | $C_{20}$ alkyl | — | — |
| 0 | $C_{13}$ alkyl | 0 | $C_{21}$ alkyl | — | — |
| 0 | $C_{13}$ alkyl | 0 | $C_{22}$ alkyl | — | — |
| 0 | $C_{14}$ alkyl | 0 | $C_{15}$ alkyl | — | — |
| 0 | $C_{14}$ alkyl | 0 | $C_{16}$ alkyl | — | — |
| 0 | $C_{14}$ alkyl | 0 | $C_{17}$ alkyl | — | — |
| 0 | $C_{14}$ alkyl | 0 | $C_{18}$ alkyl | — | — |
| 0 | $C_{14}$ alkyl | 0 | $C_{19}$ alkyl | — | — |
| 0 | $C_{14}$ alkyl | 0 | $C_{20}$ alkyl | — | — |
| 0 | $C_{14}$ alkyl | 0 | $C_{21}$ alkyl | — | — |
| 0 | $C_{14}$ alkyl | 0 | $C_{22}$ alkyl | — | — |
| 0 | $C_{15}$ alkyl | 0 | $C_{16}$ alkyl | — | — |
| 0 | $C_{15}$ alkyl | 0 | $C_{17}$ alkyl | — | — |
| 0 | $C_{15}$ alkyl | 0 | $C_{18}$ alkyl | — | — |
| 0 | $C_{15}$ alkyl | 0 | $C_{19}$ alkyl | — | — |
| 0 | $C_{15}$ alkyl | 0 | $C_{20}$ alkyl | — | — |
| 0 | $C_{15}$ alkyl | 0 | $C_{21}$ alkyl | — | — |
| 0 | $C_{15}$ alkyl | 0 | $C_{22}$ alkyl | — | — |
| 0 | $C_{16}$ alkyl | 0 | $C_{17}$ alkyl | — | — |
| 0 | $C_{16}$ alkyl | 0 | $C_{18}$ alkyl | — | — |
| 0 | $C_{16}$ alkyl | 0 | $C_{19}$ alkyl | — | — |
| 0 | $C_{16}$ alkyl | 0 | $C_{20}$ alkyl | — | — |
| 0 | $C_{16}$ alkyl | 0 | $C_{21}$ alkyl | — | — |
| 0 | $C_{16}$ alkyl | 0 | $C_{22}$ alkyl | — | — |
| 0 | $C_{17}$ alkyl | 0 | $C_{18}$ alkyl | — | — |
| 0 | $C_{17}$ alkyl | 0 | $C_{19}$ alkyl | — | — |
| 0 | $C_{17}$ alkyl | 0 | $C_{20}$ alkyl | — | — |
| 0 | $C_{17}$ alkyl | 0 | $C_{21}$ alkyl | — | — |
| 0 | $C_{17}$ alkyl | 0 | $C_{22}$ alkyl | — | — |
| 0 | $C_{18}$ alkyl | 0 | $C_{19}$ alkyl | — | — |
| 0 | $C_{18}$ alkyl | 0 | $C_{20}$ alkyl | — | — |
| 0 | $C_{18}$ alkyl | 0 | $C_{21}$ alkyl | — | — |
| 0 | $C_{18}$ alkyl | 0 | $C_{22}$ alkyl | — | — |
| 0 | $C_{19}$ alkyl | 0 | $C_{20}$ alkyl | — | — |
| 0 | $C_{19}$ alkyl | 0 | $C_{21}$ alkyl | — | — |
| 0 | $C_{19}$ alkyl | 0 | $C_{22}$ alkyl | — | — |
| 0 | $C_{20}$ alkyl | 0 | $C_{21}$ alkyl | — | — |
| 0 | $C_{20}$ alkyl | 0 | $C_{22}$ alkyl | — | — |
| 0 | $C_{21}$ alkyl | 0 | $C_{22}$ alkyl | — | — |
| 1 | $C_6$ alkyl | 1 | $C_8$ alkyl | — | — |
| 1 | $C_6$ alkyl | 1 | $C_{10}$ alkyl | — | — |
| 1 | $C_6$ alkyl | 1 | $C_{12}$ alkyl | — | — |
| 1 | $C_6$ alkyl | 1 | $C_{14}$ alkyl | — | — |
| 1 | $C_6$ alkyl | 1 | $C_{16}$ alkyl | — | — |
| 1 | $C_6$ alkyl | 1 | $C_{18}$ alkyl | — | — |
| 1 | $C_6$ alkyl | 1 | $C_{20}$ alkyl | — | — |
| 1 | $C_6$ alkyl | 1 | $C_{22}$ alkyl | — | — |

TABLE B-continued

Mixtures of Compounds Comprising Two or Three Sets of Compounds

| First set of compounds | | Second set of compounds | | Third set of compounds | |
|---|---|---|---|---|---|
| k | $R^3$ | k | $R^3$ | k | $R^3$ |
| 1 | $C_8$ alkyl | 1 | $C_{10}$ alkyl | — | — |
| 1 | $C_8$ alkyl | 1 | $C_{12}$ alkyl | — | — |
| 1 | $C_8$ alkyl | 1 | $C_{14}$ alkyl | — | — |
| 1 | $C_8$ alkyl | 1 | $C_{16}$ alkyl | — | — |
| 1 | $C_8$ alkyl | 1 | $C_{18}$ alkyl | — | — |
| 1 | $C_8$ alkyl | 1 | $C_{20}$ alkyl | — | — |
| 1 | $C_8$ alkyl | 1 | $C_{22}$ alkyl | — | — |
| 1 | $C_9$ alkyl | 1 | $C_8$ alkyl | — | — |
| 1 | $C_9$ alkyl | 1 | $C_{10}$ alkyl | — | — |
| 1 | $C_9$ alkyl | 1 | $C_{12}$ alkyl | — | — |
| 1 | $C_6$ alkyl | 1 | $C_{14}$ alkyl | — | — |
| 1 | $C_9$ alkyl | 1 | $C_{16}$ alkyl | — | — |
| 1 | $C_9$ alkyl | 1 | $C_{18}$ alkyl | — | — |
| 1 | $C_9$ alkyl | 1 | $C_{20}$ alkyl | — | — |
| 1 | $C_9$ alkyl | 1 | $C_{22}$ alkyl | — | — |
| 1 | $C_{10}$ alkyl | 1 | $C_{12}$ alkyl | — | — |
| 1 | $C_{10}$ alkyl | 1 | $C_{14}$ alkyl | — | — |
| 1 | $C_{10}$ alkyl | 1 | $C_{16}$ alkyl | — | — |
| 1 | $C_{10}$ alkyl | 1 | $C_{18}$ alkyl | — | — |
| 1 | $C_{10}$ alkyl | 1 | $C_{20}$ alkyl | — | — |
| 1 | $C_{10}$ alkyl | 1 | $C_{22}$ alkyl | — | — |
| 1 | $C_{12}$ alkyl | 1 | $C_{14}$ alkyl | — | — |
| 1 | $C_{12}$ alkyl | 1 | $C_{16}$ alkyl | — | — |
| 1 | $C_{12}$ alkyl | 1 | $C_{18}$ alkyl | — | — |
| 1 | $C_{12}$ alkyl | 1 | $C_{20}$ alkyl | — | — |
| 1 | $C_{12}$ alkyl | 1 | $C_{22}$ alkyl | — | — |
| 1 | $C_{14}$ alkyl | 1 | $C_{16}$ alkyl | — | — |
| 1 | $C_{14}$ alkyl | 1 | $C_{18}$ alkyl | — | — |
| 1 | $C_{14}$ alkyl | 1 | $C_{20}$ alkyl | — | — |
| 1 | $C_{14}$ alkyl | 1 | $C_{22}$ alkyl | — | — |
| 1 | $C_{16}$ alkyl | 1 | $C_{18}$ alkyl | — | — |
| 1 | $C_{16}$ alkyl | 1 | $C_{20}$ alkyl | — | — |
| 1 | $C_{16}$ alkyl | 1 | $C_{22}$ alkyl | — | — |
| 1 | $C_{18}$ alkyl | 1 | $C_{20}$ alkyl | — | — |
| 1 | $C_{18}$ alkyl | 1 | $C_{22}$ alkyl | — | — |
| 1 | $C_{20}$ alkyl | 1 | $C_{22}$ alkyl | — | — |
| 0 | $C_6$ alkyl | 1 | $C_6$ alkyl | — | — |
| 0 | $C_8$ alkyl | 1 | $C_8$ alkyl | — | — |
| 0 | $C_9$ alkyl | 1 | $C_9$ alkyl | — | — |
| 0 | $C_{10}$ alkyl | 1 | $C_{10}$ alkyl | — | — |
| 0 | $C_{12}$ alkyl | 1 | $C_{12}$ alkyl | — | — |
| 0 | $C_{14}$ alkyl | 1 | $C_{14}$ alkyl | — | — |
| 0 | $C_{16}$ alkyl | 1 | $C_{16}$ alkyl | — | — |
| 0 | $C_{18}$ alkyl | 1 | $C_{18}$ alkyl | — | — |
| 0 | $C_{20}$ alkyl | 1 | $C_{20}$ alkyl | — | — |
| 0 | $C_{22}$ alkyl | 1 | $C_{22}$ alkyl | — | — |
| 0 | $C_6$ alkyl | 2 | $C_6$ alkyl | — | — |
| 0 | $C_8$ alkyl | 2 | $C_8$ alkyl | — | — |
| 0 | $C_9$ alkyl | 2 | $C_9$ alkyl | — | — |
| 0 | $C_{10}$ alkyl | 2 | $C_{10}$ alkyl | — | — |
| 0 | $C_{12}$ alkyl | 2 | $C_{12}$ alkyl | — | — |
| 0 | $C_{14}$ alkyl | 2 | $C_{14}$ alkyl | — | — |
| 0 | $C_{16}$ alkyl | 2 | $C_{16}$ alkyl | — | — |
| 0 | $C_{18}$ alkyl | 2 | $C_{18}$ alkyl | — | — |
| 0 | $C_{20}$ alkyl | 2 | $C_{20}$ alkyl | — | — |
| 1 | $C_6$ alkyl | 2 | $C_6$ alkyl | — | — |
| 1 | $C_8$ alkyl | 2 | $C_8$ alkyl | — | — |
| 1 | $C_9$ alkyl | 2 | $C_9$ alkyl | — | — |
| 1 | $C_{10}$ alkyl | 2 | $C_{10}$ alkyl | — | — |
| 1 | $C_{12}$ alkyl | 2 | $C_{12}$ alkyl | — | — |
| 1 | $C_{14}$ alkyl | 2 | $C_{14}$ alkyl | — | — |
| 1 | $C_{16}$ alkyl | 2 | $C_{16}$ alkyl | — | — |
| 1 | $C_{18}$ alkyl | 2 | $C_{18}$ alkyl | — | — |
| 1 | $C_{20}$ alkyl | 2 | $C_{20}$ alkyl | — | — |
| 1 | $C_{22}$ alkyl | 2 | $C_{22}$ alkyl | — | — |
| 0 | $C_6$ alkyl | 1 | $C_6$ alkyl | 2 | $C_6$ alkyl |
| 0 | $C_8$ alkyl | 1 | $C_8$ alkyl | 2 | $C_8$ alkyl |
| 0 | $C_9$ alkyl | 1 | $C_9$ alkyl | 2 | $C_9$ alkyl |
| 0 | $C_{10}$ alkyl | 1 | $C_{10}$ alkyl | 2 | $C_{10}$ alkyl |
| 0 | $C_{12}$ alkyl | 1 | $C_{12}$ alkyl | 2 | $C_{12}$ alkyl |
| 0 | $C_{14}$ alkyl | 1 | $C_{14}$ alkyl | 2 | $C_{14}$ alkyl |
| 0 | $C_{16}$ alkyl | 1 | $C_{16}$ alkyl | 2 | $C_{16}$ alkyl |
| 0 | $C_{18}$ alkyl | 1 | $C_{18}$ alkyl | 2 | $C_{18}$ alkyl |
| 0 | $C_{20}$ alkyl | 1 | $C_{20}$ alkyl | 2 | $C_{20}$ alkyl |
| 0 | $C_{22}$ alkyl | 1 | $C_{22}$ alkyl | 2 | $C_{22}$ alkyl |

The amount of each different type of compound in the mixture can and will vary. For example, the amount of each set of compounds in the mixture may range from about 1% to about 99% of the total weight of the mixture. For example, in embodiments comprising two sets of compounds, the weight ratio of the first set to the second set may be about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. Similarly, in embodiments comprising mixtures of monomers and dimers, the weight ratio of monomers to dimers may be about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5.

The mixture of compounds may have certain advantageous properties over the individual components of the mixture. For example, a mixture of monomers, dimers, trimers, and higher order oligomers may have increased solubility or a lower CMC as compared to the individual components of the mixture.

(b) Optional Additional Agents

In some embodiments, the composition comprising a mixture of compounds may further comprise at least one agent chosen from pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, preservatives, coloring agents, fragrance agents, and combinations thereof.

In some embodiments, the composition may comprise at least one pH regulating agent. Non-limiting examples of suitable pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; organic bases (such as, for example, pyridine, triethylamine (i.e., monoethanol amine), diisopropylethylamine, N methylmorpholine, N,N dimethylaminopyridine); and combinations of any of the above.

In other embodiments, the composition may comprise at least one stain-removing enzyme. Suitable enzymes include but are not limited to proteases, peptidases, subtilisin, mannanases, amylases, carbohydrases, and lipases.

In still other embodiments, the composition may comprise at least one different type of surfactant. For example, the different surfactant may be another class of nonionic surfactant, an anionic surfactant, or a cationic surfactant. Non-limiting examples of suitable nonionic surfactants (including zwitterionic surfactants that have no net charge) include alcohol ethoxylates, alkyl phenol ethoxylates (e.g., nonylphenyl ethoxylate), thiol ethoxylates, fatty acid ethoxylates, glycerol esters, hexitol esters, amine ethoxylates, alkylamide ethoxylates, and imide ethoxylates. Suitable anionic surfactants include, but are not limited to, alkyl sulfates, alkyl ether sulfates, sulfated alkanolamides, glyceride sulfates, dodecyl benzene sulfonates, alkylbenzene sulfonates, alpha olefin sulfonates, and sulfocarboxylic compounds. Exemplary anionic surfactants include sodium dodecylbenzene sulfonate, and sodium methyl cocoyl taurate. Non-limiting examples of suitable cationic surfactants include alkyl amines, quaternary alkyl ammoniums, ester amines, and ether amines.

In further embodiments, the composition may comprise at least one optical brightener. Optical brighteners (also known as optical brightening agents, fluorescent brightening agents, or fluorescent whitening agents) are dyes that absorb light in the ultraviolet and violet region and reemit light in the blue regions. Non-limiting examples of suitable optical brightening agents include triazine-stilbenes, coumarins, imidazolines, diazoles, triazoles, benzoxazolines, and biphenyl-stilbenes. In one embodiment, the optical brightening agent may be a sulfonated tetrabenzotetraazaaporphine derivative. In some embodiments, the optical brightening agent may be used in combination with a polyol, such as polyethylene glycol, polypropylene glycol, or polyvinyl alcohol.

In still other embodiments, the composition may comprise at least one bleaching agent. Suitable bleaching agents include without limit hydrogen peroxide, peroxy acid, sodium perborate, sodium percarbonate, sodium hypochlorite, and sodium dichloroisocyanurate.

In some embodiments, the composition may comprise at least one thickening agent (or rheological additive). Suitable thickening agents include but are not limited to cellulosic ethers (such as hydroxycellulose, hydroxypropyl cellulose, hydroxymethylpropyl cellulose, hydroxyethyl cellulose, carboxymethyl cellulose, methylhydrdoxyethyl cellulose), polyvinylpyrrolidone, poly(vinylpyridine-N-oxide), bentonites, starches, gums, and combinations thereof.

In certain embodiments, the composition may comprise at least one scale inhibitor. Non-limiting examples of suitable scale inhibitors include phosphonates, sodium hexametaphosphate, sodium tripolyphosphate, oxalic acid, phosphoric acid, sulfamic acid, and carboxymethyl inulin.

In other embodiments, the composition may comprise at least one chelating agent. Suitable chelating agents include but are not limited to EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, DTPMP, and combinations thereof.

In further embodiments, the composition may comprise at least one water softening agent. Non-limiting examples of suitable water softening agents include sodium triphosphate, sodium tripolyphosphate, sodium carbonate, sodium silicate, zeolites, and citric acid.

In some embodiments, the composition may comprise at least one foam control agent, such as ethylene oxide/propylene oxide copolymers, silicone, or a particulate foam control agent such as silica.

In still other embodiments, the composition may comprise at least one dispersant. Suitable dispersants include without limit phosphonates, carboxymethyl inulin, sodium hexametaphosphate, sodium tripolyphosphate, tetrasodium pyrophosphate, potassium tripolyphosphate, acrylic polymers, and combinations thereof.

In other embodiments, the composition may comprise at least one hydrotrope. Hydrotropes are compounds that improve the solubility of surfactants in aqueous solutions. Non-limiting examples of suitable hydrotropes include sodium toluenesulfonate, potassium toluene sulfonate, sodium xylene sulfonate, potassium xylene sulfonate, ammonium xylene sulfonate, sodium cumene sulfonate, ammonium cumene sulfonate, alkyl glucoside, complex coco imino glycinate, complex coco imino dipropionate, octyl imino dipropionate, phosphate ester potassium salt, and quaternary fatty methyl amine ethoxylate.

In yet alternate embodiments, the composition may comprise at least one linker. Linkers are amphiphiles that are used to increase surfactant-water interactions (i.e., hydrophilic linkers) or surfactant-oil interactions (i.e., lipophilic linkers). Suitable hydrophilic linkers include without limit alkyl naphthalene sulfonates such as mono- or di-methyl naphthalene sulfonate and diisopropyl naphthalene sulfonate. Non-limiting examples of suitable lipophilic linkers include hydrocarbyl alcohols having 8 or more carbon atoms in the principal chain or their low ethoxylated derivatives.

In other embodiments, the composition may comprise at least one filler. Non-limiting examples of suitable fillers include cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, talc, modified starches, lactose, sucrose, mannitol, sorbitol, and combinations thereof.

In still other embodiments, the composition may comprise at least one disintegrant. Suitable disintegrants include without limit starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth, and combinations thereof.

In other embodiments, the composition may comprise at least one preservative. Non-limiting examples of suitable preservatives include antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, sodium hypochlorite, and combinations thereof.

In still other embodiments, the composition may comprise at least one coloring agent. Suitable coloring agents include, but are not limited to, food, drug and cosmetic colors (FD&C), drug and cosmetic colors (D&C), external drug and cosmetic colors (Ext. D&C), and other dyes known in the industry.

In further embodiments, the composition may comprise at least one fragrance (or perfume) agent. Suitable fragrance (or perfume) agents are well known in the art.

The weight fraction of the optional additional agents in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In various embodiments, the composition may be a liquid solution, an aqueous solution, an emulsion, a gel, a paste, a powder, a granular mixture, a pelleted mixture, or a solid.

(III) Applications and Uses Thereof

The compounds or mixtures of compounds disclosed herein may be used in a variety of applications. In general, the usefulness of the compounds or mixtures of compounds relates to their surfactant qualities. For example the compounds or mixtures of compounds disclosed herein may be used to replace alcohol ethoxylate surfactants in numerous products and/or applications.

In general, the compounds or mixtures of compounds of the invention may be used as detergents, wetting agents, solvents, emulsifiers, foaming agents, or dispersants. In some embodiments, the compounds or mixtures of compounds may be used as detergent compounds in laundry detergents, laundry pre-wash products, spot treatments, fabric softeners, automatic dishwasher detergents, hand dishwashing liquids, household detergents, household cleaners, heavy duty cleaners, solid surface cleaners, degreasers, floor cleaners, floor polishes, upholstery cleaners, auto cleaners, institutional cleaners, laboratory cleaners, detergents for biochemisty/biotechnology applications, personal care products, hand cleaners, shampoos, hair conditioners, hair styling products, hair coloring products, hair shine products, facial cleaners, body washes, shower gels, bath oils, bar soaps, bubble bath, personal wipes, baby cleaning products, toothpastes, dental gels, cosmetic products, face creams, eye creams, anti-aging creams, serums, sun protecting lotions, body lotions, hand lotions, anti-perspirants, tanning lotions, laxatives, industrial cleaners, industrial surfactants, industrial emulsifiers, industrial degreasers, paints, adhesives, inks, quantum dot coatings, anti-fog agents, ski or snowboard waxes, or oil additives. The compositions listed above may be liquids, gels, foams, emulsions, aerosols, powders, granulates, solids, and so forth.

The amount of the compound or mixtures of compounds disclosed herein included in the various compositions or uses listed above can and will vary depending upon the identity of the compound or compounds and the intended use of the composition. In general, the amount of the compound or mixtures of compounds of the invention included in a composition may range from about 0.1% to about 99.9% of the total weight of the composition. In various embodiments, the amount of the compound or mixtures of compounds of the invention included in a composition may range from about 0.1% to about 1%, from about 1% to about 3%, from about 3% to about 10%, from about 10% to about 30%, or from about 30% to about 99.9%.

In other embodiments, the compounds or mixtures of compounds may be used in a variety of applications including textile processing (e.g., pre-scouring, desizing, and/or finishing applications), wool processing, metal processing (e.g., cutting oils and water-based hydraulic fluids), agricultural applications (e.g., emulsifiable concentrates; soil wetting agents; agrochemical formulations), latex production (e.g., emulsion polymerization), paper processing, paper de-inking, oil harvesting or processing (e.g., hydraulic fracturing ("fracking") fluids, crude oil drilling fluids and demulsifiers, wetting agents, mobilization of oil in oil wells, liquid drag reducing agent in pipelines), oil reclamation processes, and enhanced oil recovery processes. Additionally, in embodiments in which $R^3$ is a short alkyl group, such compounds or mixtures of compounds may be used as solvents. For example, in some iterations in which $R^3$ is a short alkyl group, the compounds or mixtures of compounds may be polar, aprotic solvents.

In exemplary embodiments, the compounds or mixtures of compounds of the invention may replace alkyphenol ethoxylates in various applications such as in household detergents or industrial detergents. For example, the compounds or mixtures of compounds may be included in cleaning compositions or laundry detergents (e.g., see Example 15, below). In another exemplary embodiment, the compounds or mixtures of compounds disclosed herein may be used in industrial processes (e.g., oil harvesting processes, oil reclamation processes, textile processing, metal processing, wool processing, etc.).

The amount of the compound or mixture of compounds used in the various applications can and will vary. In general, the amount of the compound or mixture of compounds used in a specific application will depend upon a variety of factors, including the type of application.

(IV) Process for Cleaning an Article

Another aspect of the disclosure provides a process for cleaning an article, wherein the process comprises contacting an article with a composition comprising at least one compound of the invention. Thus, the composition may comprise at least one monomer, dimer, oligomer, or a mixture of any of the above. In some embodiments, the process may further comprise a rinsing step in which the article is contacted with water to remove the at least one compound of the invention.

In certain embodiments, the article may be an inanimate object. Non-limiting examples of suitable inanimate objects include as laundry items, dishes, flatware, cookware items, counters, floors, or other surfaces. As an example, the surface may be an oil contaminated surface, wherein the process entails removing the oil from the contaminated surface. In other embodiments, the article may be an animate object or a part of an animate object. Examples of suitable animate objects include but are not limited to hair, hands, face, and other body parts.

(V) Processes for Preparing Compounds of the Invention

Still another aspect of the present disclosure encompasses processes for the preparation of the compounds of the invention. In particular, processes are provided for preparing ester and amide compounds, i.e., compounds comprising Formulas (Ib) and (Ic), respectively. Also provided are processes that are modified to obtain mixtures of the monomeric and oligomeric compounds of the invention.

(a) Preparation of Ester Compounds via Esterification Reaction

Another aspect of the disclosure provides processes for the preparation of ester compounds such as those comprising Formula (Ib). As an example, the ester compound may be prepared via a process comprising an esterification reaction. Such a process may comprise two steps—an esterification reaction step and an oxidation reaction step in which a sulfide group is oxidized to a sulfoxide group. The two steps of the process may occur in either order (e.g., the oxidation reaction may occur before or after the esterification reaction). Reaction scheme 1 depicts the preparation of compounds comprising Formula (Ib) in accordance with a process in which the first step (Step A) comprises the esterification reaction.

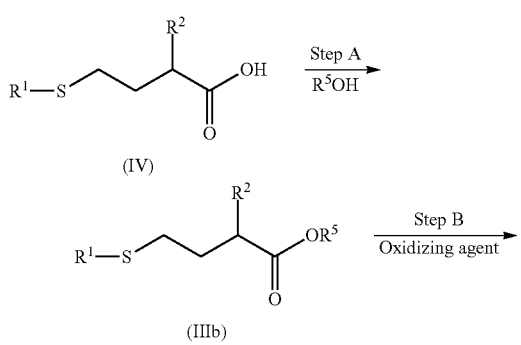

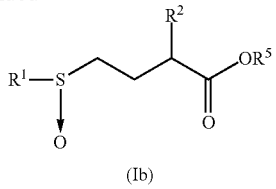

(Ib)

wherein $R^1$, $R^2$, and $R^5$ are as defined above in section (I)(a) for compounds comprising Formula (I).

(i) Esterification Reaction

The esterification step or step A of the process diagrammed above comprises contacting a compound comprising Formula (IV) with $R^5OH$ in the presence of a catalyst to form a compound comprising Formula (IIIa). The catalyst may be a chemical catalyst, such as a proton donor. Alternatively, the catalyst may be an enzyme catalyst, such as a lipase enzyme. Lipase enzymes can catalyze the formation (as well as hydrolysis) of ester linkages.

The compound comprising Formula (IV) and the $R^5OH$ compound can and will vary depending on the identity of the $R^1$, $R^2$, and $R^5$ groups, which are detailed above in section (I)(a) for compounds comprising Formula (Ib). The compound comprising Formula (IV) may be derived from natural or synthetic sources. The $R^5OH$ compound is generally a compound comprising at least one hydroxyl group. The compound comprising at least one hydroxyl group may be straight, branched, saturated, or unsaturated, and may be natural or synthetic. In exemplary embodiments, $R^5$ may be a $C_6$ to $C_{22}$ alkyl. Thus, in some embodiments $R^5OH$ may be hexanol, heptanol, octanol, $C_9$ alcohol (e.g., NEODOL 9), decanol, $C_{11}$ alcohol (e.g., NEODOL 1), dodecanol, $C_{13}$ alcohol, tetradecanol, $C_{15}$ alcohol, hexadecanol, $C_{17}$ alcohol, octadecanol, $C_{19}$ alcohol, icoanol, $C_{21}$ alcohol, docosanol, or combinations thereof.

The mole-to-mole ratio of the compound comprising Formula (IV) to $R^5OH$ may vary. In general, the mole-to-mole ratio of the compound comprising Formula (IV) to $R^5OH$ may range from about 1:1 to about 1:5. In various embodiments, the mole-to-mole ratio of the compound comprising Formula (IV) to $R^5OH$ may be about 1:1.0, 1:1.1, 1:1.2, 1:1.3, 1:1.4, 1:1.5, 1:1.6, 1:1.7, 1:1.8, 1:2.0. In a preferred embodiment, the mole-to-mole ratio of the compound comprising Formula (IV) to $R^5OH$ may be about 1:1.5.

Chemical catalyst. In some embodiments, the catalyst may be a proton donor. A variety of proton donors may be used in the process. Non-limiting examples of suitable proton donor include acid salts (e.g., sodium or potassium bicarbonates, bisulfates, hydrosulfates, or phosphates), mineral acids (e.g., hydrogen halides such as hydrochloric acid, hydrobromic acid; halogen oxoacids such as hypochloric acid, chloric acid, perchloric acid, periodic acid; sulfuric acid; boric acid; nitric acid, phosphoric acid, etc.); sulfonic acids (e.g., methanesulfonic acid, p-toluenesulfonic acid); solid bound proton donors (e.g., Amberlyst 15, Amberlyst 35, and the like); ion exchange resins (e.g., Amberlite, Amberjet, Dowex, etc.); ionomers (e.g., polystyrene sulfonate, Nafion, Hycar and so forth); and ionic liquids having acidic characteristics. In an exemplary embodiment, the proton donor may be sodium bisulfate.

The mole-to-mole ratio of the compound comprising Formula (IV) to the proton donor can and will vary depending upon the identity of the proton donor. In general, the mole-to-mole ratio of the compound comprising Formula (IV) to the proton donor may range from about 1:0.005 to about 1:0.1. In some embodiments, the mole-to-mole ratio of the compound comprising Formula (IV) to the proton donor may be about 1:0.01, 1:0.015, 1:0.02, 1:0.025, 1:0.03, 1:0.035, 1:0.04, or 1:0.05. In a preferred embodiment, the mole-to-mole ratio of the compound comprising Formula (IV) to the proton donor may be 1:0.02.

Enzymatic catalyst. In other embodiments, the catalyst may be an enzyme. For example, the enzyme may be a lipase. The lipase may be of microbial origin or animal origin (e.g., calf sublingual gland extract or pancreas extract). In exemplary embodiments, the lipase may be microbial and may be from *Aspergillus niger* (e.g., Lipase AS"Amano;" Lipase A"Amano"6), *Burkholderia cepacia*, *Candida antarctica* (e.g., Lipase B, Novozyme 435®), *Candida rugosa* (e.g., Lipase AY "Amano"30; Lipase AYS"Amano"), *Candida cylindracea*, *Candida lipolytica*, *Mucor javanicus* (e.g., Lipase A"Amano"10), *Penciffium camembertii* (e.g., Lipase G"Amano"50), *Penicillium roqueforti* (e.g., Lipase R"Amano"), *Pseudomonas cepacia* (e.g., Lipase PS"Amano"), *Pseudomonas fluorescens* (e.g., Lipase AK"Amano"), *Pseudomonas* sp. (e.g., Lipase "Amano"2, Lipase "Amano"3), *Rhizomucor miehei*, *Rhizopus oryzae* (e.g., Lipase F-AP15), *Rhizopus niveus* (e.g., Newlase F, Newlase F3G). In an exemplary embodiment, the lipase may be Lipase B from *Candida antarctica* (i.e., Novozyme 435®)

The lipase may be in free form (e.g., a powder, a liquid solution, etc.) or the lipase may be immobilized. For example, the lipase may be immobilized on a solid phase. Nonlimiting examples of suitable solid phases include silica, silica gel, diatomaceous earth, clays, ceramics, alumina, zeolites, aluminum oxides, glass, metal oxides, hydroxyapatite, a polymer (e.g., cellulose, cellulose ethers, dextrans, Sephadex, agarose, polypropylene, polyethylene, polystyrene, polyalkylene oxides, nylon, and the like). The solid phase may comprise beads, particles, granules, gel, membrane, woven mat, fibers, and so forth. Immobilized enzymes may be recycled and used repeatedly.

The amount of lipase included in the reaction can and will vary depending upon the activity of the enzyme and the identity of the substrates in the reaction. For example, the amount of lipase may range from about 1 wt % to about 50 wt % of the total reaction. In one exemplary embodiment, about 20 wt % of immobilized *C. antarctica* Lipase B is added to the reaction mixture.

In some embodiments, the esterification reaction is conducted without a solvent. In other embodiments, the esterification reaction is performed in the presence of a solvent. The type of solvent may vary depending upon the identity of the reactants. Thus, the solvent may be a nonpolar solvent, a protic polar solvent, an aprotic polar solvent, or a combination thereof. Non-limiting examples of suitable nonpolar solvents include benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Examples of suitable protic polar solvents include without limit water, alcohols (e.g., methanol, ethanol, isopropanol, n-propanol, isobutanol, n-butanol, s-butanol, t-butanol), diols (e.g., propylene glycol and the like), organic acids (e.g., formic acid, acetic acid, and so forth), amides (e.g., formamide, acetamide, and the like), and combinations of any of the above. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3- dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In one exemplary embodiment, the solvent used in Step A of the process may be toluene.

The weight-to-weight ratio of the solvent to the compound comprising Formula (IV) can and will vary. Typically, the weight-to-weight ratio of the solvent to the compound comprising Formula (IV) may range from about 1:1 to about 1000:1. In various embodiments, the weight-to-weight ratio of the solvent to the compound comprising Formula (IV) may range from about 1:1 to about 3:1, from about 3:1 to about 10:1, from about 10:1 to about 30:1, or from about 30:1 to about 100:1. In preferred embodiments, the weight-to-weight ratio of the solvent to the compound comprising Formula (IV) may range from about 3:1 to about 10:1.

The esterification reaction may be conducted at a temperature that ranges from about 30° C. to about 200° C. In certain embodiments, the temperature of the reaction may be about 40, 50, 60, 70, 80, 90, 100, 110, 120, 130, 140, 150° C. In preferred embodiments, the reaction may be conducted at a temperature from about 100-115° C. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed for about 2 hours, from about 4 to about 6 hours, or from about 12 to about 18 hours. Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compound comprising Formula (IV) and a significantly increased amount of the compound comprising Formula (IIIb) compared to the amounts of each present at the beginning of the reaction.

The compound comprising Formula (IIIb) may be isolated from the reactants in the reaction mixture by means known in the art. Suitable means include extracting, washing, precipitating, filtering, distilling, evaporating, drying, chromatography, and combinations thereof. In exemplary embodiments, the compound comprising Formula (IIIb) may be isolated via chromatography.

The yield of the compound comprising Formula (IIIb) can and will vary. In general, yield of the compound comprising Formula (IIIb) will be at least about 30%, at least about 40%, at least about 50%, at least about 60%, at least about 70%, at least about 80%, or at least about 90%.

(ii) Oxidation Reaction

The oxidation reaction or step B of the process diagrammed above in Reaction Scheme 1 comprises contacting the compound comprising Formula (IIIb) with an oxidizing agent to form the compound comprising Formula (Ib). A variety of oxidizing agents may be used in this step of the process. Non-limiting examples of suitable oxidizing agents include peroxy acids (e.g., chloroperoxybenzoic acid, peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benezeneselenic acid, lead tetraacetate, osmium tetroxide, phosphomolybdic acid hydrate, pyridinium chlorochromate, pyridinium dichromate, quinolinium dichromate, and the like).and combinations thereof. In preferred embodiment, the oxidizing agent may be m-chloroperoxybenzoic acid or hydrogen peroxide.

The mole-to-mole ratio of the compound comprising Formula (IIIb) to the oxidizing agent can and will vary. In general, the mole-to-mole ratio of the compound comprising Formula (IIIb) to the oxidizing agent may range from about 1:0.1 to about 1:20. In various embodiments, the mole-to-mole ratio of the compound comprising Formula (IIIb) to the oxidizing agent may be about 1:0.8, 1:1.0, 1:1.2, 1:1.4, 1:1.6, 1:1.8, 1:2.0, 1;2.2, 1:2.4, 1:2.6, 1:2.8, 1:3.0, 1:3.2, 1:3.4, 1:3.6, 1:3.8, or 1:4.0. In preferred embodiments, the mole-to-mole ratio of the compound comprising Formula (IIIb) to the oxidizing agent may be range from about 1:1 to about 1:3.

The oxidation reaction may be performed in the presence of a solvent. The solvent may be a nonpolar solvent, a protic solvent, or an aprotic solvent depending upon the nature of the reactants. Suitable solvents are detailed above in section (V)(a)(i). In preferred embodiments, the solvent may be dichloromethane, methanol, or water.

The weight-to-weight ratio of the solvent to the compound comprising Formula (IIIb) can and will vary. Typically, the weight-to-weight ratio of the solvent to the compound comprising Formula (IIIb) may range from about 1:1 to about 50:1. In various embodiments, the weight-to-weight ratio of the solvent to the compound comprising Formula (IIIb) may be about 2:1, 3:1, 4:1, 5:1, 6:1, 8:1, 10:1, 12:1, 15:1, 17:1, 20:1, 22:1, 25:1, 27:1, 30:1, 32:1, 35:1, 37:1, 40:1, 42:1, or 45:1. In preferred embodiments, the weight-to-weight ratio of the solvent to the compound comprising Formula (IIIb) may be about 4:1, 20:1, 30:1, or 40:1.

The oxidation reaction may be conducted at a temperature that ranges from about −10° C. to about 50° C. In certain embodiments, the temperature of the reaction maybe about 0, 10, 20, 25, or 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art. In this context, the final reaction mixture contains a significantly diminished amount of the compound comprising Formula (IIIb) and a significantly increased amount of the compound comprising Formula (Ib) compared to the amounts of each present at the beginning of the reaction.

The compound comprising Formula (Ib) may be isolated from the reactants in the reaction mixture by means well known in the art. Suitable means include extracting, washing, precipitating, filtering, distilling, evaporating, drying, chromatography, chiral chromatography, and combinations thereof. In exemplary embodiments, the compound comprising Formula (Ib) may be isolated using chromatography.

The yield of the compound comprising Formula (Ib) can and will vary. In general, yield of the compound comprising Formula (Ib) will be at least about 40%, at least about 50%, at least about 60%, at least about 70%, at least about 80%, at least about 90%, at least about 95%, at least about 96%, at least about 97%, at least about 98%, or at least about 99%.

(b) Preparation of Ester Compounds via Alternate Methods

In other embodiments, compounds comprising Formula (Ib) may be prepared via an esterification reaction as detailed above, except the hydroxyl of the carboxylic acid group of the compound comprising (IV) is replace with a halogen such as chlorine, bromine, fluorine, or iodine.

In still other embodiments, compounds comprising Formula (Ib) may be prepared via a process comprising a transesterification reaction. Thus, the process consists of a transesterification reaction step and an oxidation reaction step, wherein the two steps may proceed in either order. In such embodiments, however, the compound comprising Formula (IV) comprises R' rather than hydrogen on the non carbonyl oxygen. In general, R' is hydrocarbyl or substituted hydrocarbyl. In various embodiments, R' may be alkyl, substituted alkyl, alkenyl, substituted alkenyl, aryl, substituted aryl, and the like. In exemplary embodiments, R' may be an alkyl such as methyl, ethyl, propyl, butyl, wherein the alkyl may be linear or branched. During the transesterification reaction, R' is exchanged with $R^5$ in the $R^5OH$ compound in the presence of a transesterification catalyst. The transesterification catalyst may be a chemical catalyst or an enzyme catalyst. In some embodiments, the chemical catalyst may be a proton donor, of which suitable examples are detailed above. In other embodiments, the chemical catalyst may be a proton acceptor. Non-limiting examples of suitable proton acceptors include hydroxides of alkali metals and alkaline earth metals (such as, for example, NaOH and Ca(OH)$_2$ and the like); metal alkoxides (such as, for example, sodium methoxide, potassium methoxide, sodium ethoxide, and so forth); group 1 salts of carbanions; amides; hydrides (such as, for example, butyl lithium, sodium amide (NaNH$_2$), sodium hydride (NaH), and the like); and combinations thereof. In still further embodiments, the transesterification catalyst may be an enzyme, such as a lipase enzyme as detailed above.

(c) Preparation of Amide Compounds

Also provided are processes for the preparation of amide compounds such as those comprising Formula (Ic). An exemplary process comprises two steps: an amidation reaction step and an oxidation reaction step, wherein the two steps of the process may proceed in either order. In some embodiments, the amidation and oxidation step are preceded by an activation step in which a leaving group is added to the carboxylic acid. Reaction scheme 2 diagrams the preparation of compounds comprising Formula (Ic) in accordance with a process in which the amidation reaction occurs before the oxidation step.

Reaction Scheme 2

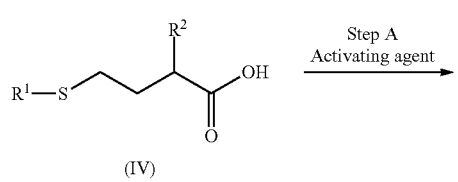

(IV)

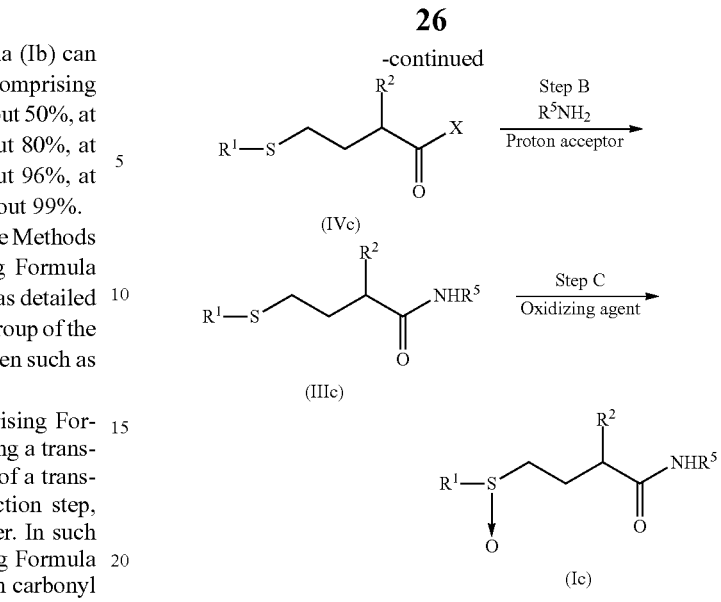

wherein $R^1$, $R^2$, and $R^5$ are as defined above in section (I)(a) for compounds comprising Formula (I) and X is a leaving group.

(i) Activation Step

The activation step or step A of the process diagrammed above comprises contacting a compound comprising Formula (IV) with an activating agent to form the compound comprising Formula (IVc). The compound comprising Formula (IV) can and will vary depending on the identity of the $R^1$, $R^2$, and $R^5$ groups, which are detailed above in section (I)(a) for compounds comprising Formula (Ic). The compound comprising Formula (IV) may be derived from natural or synthetic sources.

A variety of activating agents may be used in Step A. Non-limiting examples of suitable activating agents include thionyl halides (e.g., thionyl chloride, thionyl bromide, thionyl fluoride), acyl halides, acyl azides, anhydrides (e.g., carboxylic anhydrides, carbonic anhydrides, N-carboxy anhydrides), ester (e.g., alkyl esters, succinimidyl esters), and combinations thereof. In a preferred embodiment, the activating agent may be thionyl chloride.

The mole-to-mole ratio of the compound comprising Formula (IV) to the activating agent can and will vary. In general, the mole-to-mole ratio of the compound comprising Formula (IV) to the activating agent may range from about 1:1 to about 1:20. In various embodiments, the mole-to-mole ratio of the compound comprising Formula (IV) to the activating agent may be about 1:2, 1:3, 1:4, 1:5, 1:6, 1:7, 1:8, 1:9, or 1:10. In a preferred embodiment, the mole-to-mole ratio of the compound comprising Formula (IV) to the activating agent may be about 1:5.

Contact with the activating agent may occur in the presence of a solvent. In general, the type of solvent used will depend upon the identity of the compound comprising Formula (IV). Suitable nonpolar, aprotic, and protic solvents are detailed above in section (V)(a)(i). Typically, the weight-to-weight ratio of the solvent to the compound comprising Formula (IV) may range from about 1:1 to about 50:1. In preferred embodiment, the weight-to-weight ratio of the solvent to the compound comprising Formula (IV) may range from about 4:1 to about 30:1.

Contact with the activating agent may occur at a temperature that ranges from about −10° C. to about 50° C. In certain embodiments, the temperature of the reaction may be about 0, 10, 20, 25, or 30° C. In one preferred embodiment, the reaction may be allowed to proceed at about 0° C. In another preferred embodiment, the temperature of the reaction may be room temperature. In another preferred embodiment, the reaction may be allowed to proceed for a first period of time at 0° C. and a second period of time at room temperature. Typically, the reaction will be conducted at atmospheric pressure.

The period of time of contact with the activating agent can and will vary. In general, the duration of time may range from about 0.5 hour to about 10 hours. In various embodiments, duration of the reaction may be about 1, 1.5, 3, 2.5, 3, 3.5, 4, 4.5 or 5 hours.

Upon completion of the reaction, a portion of the solvent may be removed from the reaction mixture using methods known to those skilled in the art.

In embodiments in which $R^2$ is OH or $NH_2$, the compound comprising Formula (IV) may undergo a protection reaction prior to the activation step. During the protection reaction, the alcohol or amine group is protected with a protecting group. Suitable protecting groups and means for attaching the protecting group are well known in the art. A variety of protecting groups and the synthesis thereof may be found in "Protective Groups in Organic Synthesis" by T. W. Greene and P. G. M. Wuts, John Wiley & Sons, 2006.

(ii) Amidation Reaction

The amidation reaction or step B of the process diagrammed above in Reaction Scheme 2 comprises contacting the compound comprising Formula (IVc) with $R^5NH_2$ in the presence of a proton acceptor. The $R^5NH_2$ compound may be derived from natural or synthetic sources. As detailed above in section (I)(a), in exemplary embodiments, $R^5$ may be $C_6$ to $C_{22}$ alkyl. Thus, in various embodiments, $R^5NH_2$ may be hexylamine, heptylamine, octylamine, $C_9$ alkyl amine, decylamine, $C_{11}$ alkyl amine, dodecylamine, $C_{13}$ alkyl amine, tetradecylamine, $C_{15}$ alkyl amine, hexadecylamine, $C_{17}$ alkyl amine, octadecylamine, $C_{19}$ alkyl amine, $C_{20}$ alkyl amine, $C_{21}$ alkyl amine, or $C_{22}$ alkyl amine. The mole-to-mole ratio of the compound comprising Formula (IVc) and $R^5NH_2$ may range from 1:0.1 to about 1:10. In preferred embodiment, the mole-to-mole ratio of the compound comprising Formula (IVc) and $R^5NH_2$ may be about 1:1.

A variety of proton acceptors are suitable for use in this reaction. Non-limiting examples of suitable proton acceptors include borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2CO_3$, $K_2OC_3$, $Li_2CO_3$, and the like), amines (such as, for example methylamine, dimethylamine, trimethylamine, ethylamine, diethylamine, triethylamine, propylamine, isopropylamine, diisopropylethylamine, and the like), organic bases (such as, for example, pyridine, N methylmorpholine, N,N dimethylaminopyridine), and mixtures of any of the above. In preferred embodiment, the proton acceptor may be triethylamine.

The mole-to-mole ratio of the compound comprising Formula (IVc) to the proton acceptor can and will vary depending upon the identity of the proton acceptor. In general, the mole-to-mole ratio of the compound comprising Formula (IVc) to the proton acceptor may range from about 1:0.01 to about 1:10. In various embodiments, the mole-to-mole ratio of the compound comprising Formula (IVc) to the proton acceptor may be about 1:0.5, 1:0.1, 1:0.5, 1:1, 1:1.5, 1:2, 1:3, 1:4, or 1:5. In a preferred embodiment, the mole-to-mole ratio of the compound comprising Formula (IVc) to the proton acceptor may be about 1:2.

The amidation reaction may be conducted at a temperature that ranges from about -10° C. to about 50° C. In certain embodiments, the reaction may be allowed to proceed at about 0, 10, 20, 25, or 30° C. In a preferred embodiment, the reaction may commence at about 0° C. and slowly warm to room temperature over a period of time. In general, the reaction will be conducted at atmospheric pressure.

The duration of the reaction can and will vary. In general, the reaction may be allowed to proceed overnight (about 15-18 hours). Typically, however, the reaction may be allowed to proceed for a sufficient period of time until the reaction is complete, as determined by means well known to those of skill in the art.

The compound comprising Formula (IIIc) may be isolated from the reaction mixture by means well known in the art. Suitable means include extracting, washing, precipitating, filtering, distilling, evaporating, drying, chromatography, and combinations thereof. In exemplary embodiments, the compound comprising Formula (IIIc) is isolated using chromatography.

The yield of the compound comprising Formula (IIIc) can and will vary. In general, yield of the compound comprising Formula (IIIc) will be at least about 30%, at least about 40%, at least about 50%, at least about 60%, at least about 70%, at least about 80%, or at least about 90%.

(iii) Oxidation Reaction

The oxidation reaction or step C of the process diagrammed in Reaction Scheme 2 comprises contacting the compound comprising Formula (IIIc) with an oxidizing agent to form the compound comprising Formula (Ic). Suitable oxidizing agents, as well as suitable amounts of oxidizing agents, solvents, and other reaction conditions are detailed above in section (V)(a)(ii).

In embodiments in which the compound comprising Formula (IV) underwent a protecting reaction prior to the activation step, the protecting group generally will be removed prior to or after the oxidation step using techniques well known in the art.

The compound comprising Formula (Ic) may be isolated from the reactants in the reaction mixture by means well known in the art. Suitable means include extracting, washing, precipitating, filtering, distilling, evaporating, drying, chromatography, and combinations thereof. In exemplary embodiments, the compound comprising Formula (Ic) is isolated using a chromatographic technique.

The yield of the compound comprising Formula (Ic) can and will vary. In general, the yield of the compound comprising Formula (Ic) will be at least about 40%, at least about 50%, at least about 60%, at least about 70%, at least about 80%, at least about 90%, at least about 95%, at least about 96%, at least about 97%, at least about 98%, or at least about 99%.

(d) Modified Processes to Obtain Mixtures of Monomer and Oligomer Compounds

The above described synthetic processes may be modified to obtain mixtures of monomers, dimers, trimers, and higher order oligomers (e.g., compounds comprising Formula (II) in which k is 0, compounds comprising Formula (II) in which k is 1, and compounds comprising Formula (II) in which k is greater than 1). For example, upon completion of an esterification reaction, the reaction mixture comprises monomer, dimer, trimer, and higher order oligomer ester compounds. Rather than isolate monomer or dimer compounds from the reaction mixture, for example, the entire mixture of compounds may be subjected to the oxidation reaction thereby preparing a mixture of compounds comprising Formula (II) in which k varies. (See Examples 16 and 17 below.) Mixtures of monomeric and oligomeric amide compounds may be formed in a similar manner by performing the amidation and oxidation reactions in a single reaction vessel without isolating intermediate compounds.

Moreover, the esterification reaction of the process, for example, may be modified such that a mixture of two or more alcohols (i.e., $R^5OH$) may be contacted with the compound comprising Formula (IV) such that the final reaction mixture comprises a mixture of ester compounds comprising different $R^5$ groups. (See Example 15 below.) Similarly, the amidation reaction may be modified to include a mixture of different amines (i.e., $R^5NH_2$) such that the final reaction mixture comprises a mixture of amide compounds comprising different $R^5$ groups.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2=CH—CH_2$—), but also to compounds that contain substituted allyl groups or allyl groups forming part of a ring system.

The term "alkyl" as used herein describes groups containing from one to thirty carbon atoms in the principal chain. They may be straight or branched chain or cyclic and include methyl, ethyl, propyl, isopropyl, butyl, hexyl and the like.

The term "alkenyl" as used herein describes groups containing from two to thirty carbon atoms in the principal chain and further comprising at least one carbon-carbon double bond. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups containing from two to thirty carbon atoms in the principal chain and further comprising at least one carbon-carbon triple bond. They may be straight or branched chain and include ethynyl, propynyl, butynyl, isobutynyl, hexynyl, and the like.

The term "amide" as used herein describes a compound comprising a carbonyl-nitrogen linkage.

The term "aminoacyl" refers to an amino acid residue.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, piperidyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic.

The term "protecting group" as used herein denotes a group capable of protecting a functional group (e.g., an alcohol or an amine), wherein the protecting group may be removed, subsequent to the reaction for which protection is employed, without disturbing the remainder of the molecule. Non-limiting examples of suitable alcohol protecting groups include acetyl (Ac), benzoyl (Bz), benzyl (Bn, Bnl), β-methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), trityl (triphenylmethyl, Tr), silyl ethers (e.g., trimethylsilyl (TMS), tert-butyldimethylsilyl (TBDMS), tri-iso-propylsilyloxymethyl (TOM), and triisopropylsilyl (TIPS) ethers), methyl ethers, and ethoxyethyl ethers (EE) and the like. Suitable amine protecting groups include without limit carbobenzyloxy (Cbz); p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts), and other sulfonamides (e.g., Nosyl & Nps), and the like. A variety of protecting groups and the synthesis thereof may be found in "Protective Groups in Organic Synthesis" by T. W. Greene and P. G. M. Wuts, John Wiley & Sons, 2006.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

A "sulfoxide" refers to a compound containing a "sulfinyl" functional group that is attached to two carbon atoms. The sulfinyl group, as depicted as:

represents:

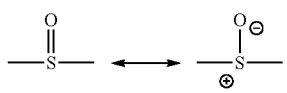

Having described the invention in detail, it will be apparent that modifications and variations are possible without departing from the scope of the invention defined in the appended claims.

EXAMPLES

The following examples illustrate various embodiments of the invention.

Example 1

Preparation of Hexyl 2-Hydroxy-4-(Methylsulfinyl)butanoate

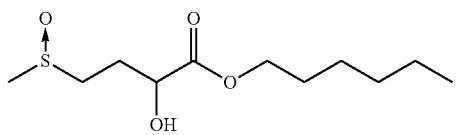 [SMILES: CCCCCCOC(=O)C(O)CCS(C)=O]

Step 1: Synthesis of hexyl 2-hydroxy-4-(methylthio)butanoate. To a 4 neck 1 L round bottom flask fitted with a reflux condenser, dean stark trap, thermocouple, and mechanical overhead stirrer was added 2-hydroxy-4-(methylthio)butanoic acid (100 g, 666 mmol, obtained for example by stirring Alimet over activated charcoal, filtering and concentrating in a rotovap), 1-hexanol (125.4 mL, 999 mmol), sodium hydrogen sulfate (1.60 g, 13.32 mmol), and toluene (500 mL). The reaction was heated to reflux with removal of water (20 mL) during the course of about 5.5 hours and the reaction was monitored by GC analysis. The reaction was cooled to room temperature overnight and the organic layer was washed with saturated NaHCO$_3$ (1×250 mL), DI water (1×250 mL) and brine (2×250 mL), dried over sodium sulfate, filtered and evaporated to give a brown oil (253.3 g). The oil was purified by kugelrohr distillation at 100° C. and 0.1 Torr vacuum to give a colorless oil (100.0 g, 64.1%). m/z 257 (MNa$^+$).

Step 2: Synthesis of hexyl 2-hydroxy-4-(methylsulfinyl) butanoate. To a solution of hexyl 2-hydroxy-4-(methylthio) butanoate (5.03 g, 21.46 mmol) in dichloromethane at 0° C. was added m-chloroperoxybenzoic acid (mCPBA) portionwise over 20 min. The resulting mixture was allowed to warm to room temperature with stirring overnight. The reaction was washed with saturated sodium bicarbonate (3×100 mL), 1N HCl (1×80 mL), and brine (1×80 mL). The organic layer was dried over magnesium sulfate, filtered and evaporated to give ~6 g of a crude oil. The oil was purified by silica gel chromatography with 0-6% methanol/dichloromethane to give an oil (4.10 g, 76%). $^1$H NMR (500 MHz, chloroform-d) δ ppm 0.89 (t, J=6.68 Hz, 3 H) 1.25-1.39 (m, 6 H) 1.67 (quin, J=6.99 Hz, 2 H) 2.05-2.17 (m, 1 H) 2.32-2.42 (m, 1 H) 2.56-2.63 (m, 3 H) 2.72-2.97 (m, 2 H) 3.34-3.44 (m, 1 H) 4.15-4.24 (m, 2 H) 4.26-4.36 (m, 1 H). m/z 251 (MH$^+$).

Example 2

Preparation of Octyl 2-Hydroxy-4-(Methylsulfinyl)butanoate

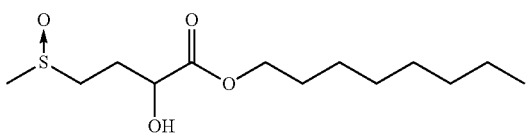 [SMILES: CCCCCCCCOC(=O)C(O)CCS(C)=O]

Step 1: Synthesis of octyl 2-hydroxy-4-(methylthio)butanoate. To a multi-neck 5 L round bottom flask fitted with a mechanical stirrer, reflux condenser, and dean stark trap was added 2-hydroxy-4-(methylthio)butanoic acid (650 g, 4.33 mol, obtained for example by stirring Alimet over activated charcoal, filtering and concentrating in a rotovap), 1-octanol (845.4 g, 6.49 mol), sodium hydrogen sulfate (10.4 g, 86 mmol), and toluene (2.7 L).The resulting solution was heated to reflux with removal of water (~146 mL) during the course of about 5.5 hours and the reaction was monitored by GC analysis. The reaction was cooled to room temperature overnight and then washed with saturated NaHCO$_3$ (1×1.5 L), DI water (1×1.5 L) and brine (1×1.5 L), dried over sodium sulfate, filtered and evaporated to give a dark oil (1,525 g). The oil was purified by kugelrohr distillation at 130-150° C. and 0.1 mm Hg vacuum to give a pale yellow oil (507.6 g, 45%). m/z 285 (MNa$^+$).

Step 2: Synthesis of octyl 2-hydroxy-4-(methylthio)butanoate. To a mixture of octyl 2-hydroxy-4-(methylthio)butanoate (50 g, 191 mmol) suspended in water (100 mL) was added 30% hydrogen peroxide (29 mL) and the mixture was stirred at 25° C. A mild exotherm was observed. The mixture became homogenous within an hour. Analysis indicated the reaction was completed within four hours. The mixture was extracted with EtOAc (200 mL). The organic phase was washed with a 10% sodium bisulfite solution (50 mL). The organic phase was dried with anhydrous magnesium sulfate and the solvent was removed by distillation with a rotary evaporator to give a colorless viscous liquid (51.4 g, 97%). $^1$H NMR (500 MHz, DMSO-$d_6$) δ ppm 0.87 (t, J=6.68 Hz, 3 H) 1.14-1.38 (m, 10 H) 1.49-1.69 (m, 2 H) 1.77-1.96 (m, 1 H) 1.96-2.17 (m, 1 H) 2.43-2.61 (m, 4 H) 2.63-2.76 (m, 1 H) 2.77-2.90 (m, 1 H) 3.96-4.13 (m, 2 H) 4.13-4.29 (m, 1 H) 5.64 (dd, J=5.72, 2.23 Hz, 1 H). m/z 279 (MH$^+$).

Example 3

Preparation of Decyl 2-Hydroxy-4-(Methylsulfinyl)butanoate

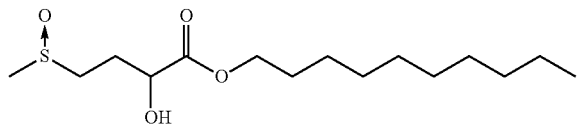 [SMILES: CCCCCCCCCCOC(=O)C(O)CCS(C)=O]

Step 1: Synthesis of decyl 2-hydroxy-4-(methylthio)butanoate. To a 4 neck 1 L round bottom flask fitted with a reflux condenser, dean stark trap, thermocouple, and mechanical overhead stirrer was added 2-hydroxy-4-(methylthio)butanoic acid (125 g, 832.2 mmol, obtained for example by stirring Alimet over activated charcoal, filtering and concentrating in a rotovap), 1-decanol (238 mL, 1248 mmol), sodium hydrogen sulfate (1.998 g, 16.64 mmol), and toluene (625 mL). The reaction was heated to reflux with removal of water (16 mL) during the course of about 6 hours and the reaction was monitored by GC analysis. The reaction was cooled to room temperature overnight and the organic layer was washed with saturated NaHCO$_3$ (1×300 mL), DI water (1×300 mL) and brine (2×300 mL), dried over sodium sulfate, filtered and evaporated to give an amber oil (395.5 g). The oil was purified by kugelrohr distillation at 110° C. and 0.1 Torr vacuum to give an oil (105.23 g, 43.5%). m/z 313 (MNa$^+$);

Step 2: Synthesis of decyl 2-hydroxy-4-(methylsulfinyl) butanoate. To a solution of decyl 2-hydroxy-4-(methylthio) butanoate (20.05 g, 69.03 mmol) in dichloromethane (300 mL) at 0° C. was added mCPBA (77%, 14.7 g, 65.6 mmol) portionwise over 30 min. The resulting mixture was allowed to warm to room temperature with stirring overnight. Another portion of mCPBA (77%, 1.4 g, 6.25 mmol) was added to the solution at 0° C. and the resulting mixture was allowed to warm to room temperature with stirring over the weekend. The reaction was washed with 10% sodium bisulfite (2×100 mL), saturated sodium bicarbonate (3×150 mL), 1N HCl (1×150 mL), and brine (1×200 mL). The organic layer was dried over magnesium sulfate, filtered and evaporated to give a crude oil. The oil was purified by silica gel chromatography with 0-6% methanol/dichloromethane to give a light yellow oil (20.61 g, 97%). $^1$H NMR (500 MHz, DMSO-$d_6$) δ ppm 0.85 (t, J=6.83 Hz, 3 H) 1.10-1.37 (m, 14 H) 1.50-1.65 (m, 2 H) 1.80-1.93 (m, 1 H) 1.97-2.08 (m, 1 H) 2.52 (d, J=3.81 Hz, 3 H) 2.60-2.75 (m, 1 H) 2.75-2.91 (m, 1 H) 3.98-4.12 (m, 2 H) 4.12-4.20 (m, 1 H) 5.62 (dd, J=5.72, 2.54 Hz, 1 H). m/z 307 (MH$^+$).

Example 4

Preparation of Dodecyl 2-Hydroxy-4-(Methylsulfinyl)butanoate

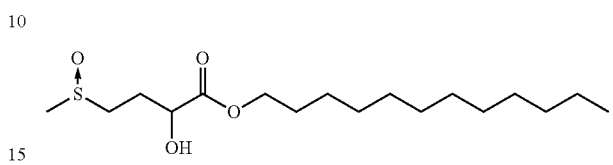

Step 1: Synthesis of dodecyl 2-hydroxy-4-(methylthio)butanoate. To a 4 neck 1 L round bottom flask fitted with a reflux condenser, dean stark trap, thermocouple, and mechanical overhead stirrer was added 2-hydroxy-4-(methylthio)butanoic acid (150 g, 999 mmol, obtained for example by stirring Alimet over activated charcoal, filtering and concentrating in a rotovap), 1-dodecanol (335 mL, 1498 mmol), sodium hydrogen sulfate (2.40 g, 19.97 mmol) and toluene (625 mL). The reaction was heated to reflux with removal of water (19 mL) during the course of about 5.5 hours and the reaction was monitored by GC analysis. The reaction was cooled to room temperature overnight and then the organic layer was washed with saturated NaHCO$_3$ (1×300 mL) and a white solid formed which was filtered. The organic layer was washed with water (1×300 mL) and brine (2×300 mL), dried over sodium sulfate, filtered and evaporated to give an amber oil (487 g). The oil was purified by kugelrohr distillation at 135° C. and 0.1 Torr vacuum to give an oil (133.18 g, 42%). m/z 341 (MNa$^+$).

Step 2: Synthesis of dodecyl 2-hydroxy-4-(methylsulfinyl) butanoate. To a solution of dodecyl 2-hydroxy-4-(methylthio) butanoate (20 g, 62.8 mmol) in methanol (100 mL) was added 30% hydrogen peroxide (20.0 mL, 176 mmol) at 0° C. The ice bath was removed and the reaction was stirred at room temperature for about 3 hrs. The reaction was mildly exothermic. Analysis indicated the reaction was completed within two hours. Water (400 mL) was added to the mixture. The mixture was extracted with EtOAc (2×100 mL). The extracts were combined and washed with a 10% sodium bisulfite solution (100 mL). The organic phase was dried with anhydrous magnesium sulfate and the solvent was evaporated with a rotary evaporator. A colorless viscous liquid was obtained which solidified upon standing to give a white solid (20.6 g, 98%). $^1$H NMR (500 MHz, DMSO-$d_6$) δ ppm 0.86 (t, J=6.83 Hz, 3 H) 1.20-1.34 (m, 18 H) 1.53-1.62 (m, 2 H) 1.81-1.92 (m, 1 H) 1.98-2.07 (m, 1 H) 2.53 (d, J=4.13 Hz, 3 H) 2.60-2.90 (m, 2 H) 3.99-4.11 (m, 2 H) 4.12-4.19 (m, 1 H) 5.63 (dd, J=5.88, 2.38 Hz, 1 H). m/z 335 (MH$^+$).

Example 5

Preparation of Octadecyl 2-Hydroxy-4-(Methylsulfinyl)butanoate

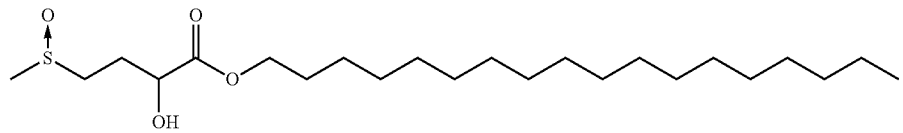 [SMILES: CCCCCCCCCCCCCCCCCCOC(=O)C(O)CCS(C)=O]

Step 1: Synthesis of octadecyl 2-hydroxy-4-(methylthio) butanoate. To a 3 neck 3 L round bottom flask fitted with a reflux condenser, dean stark trap, thermocouple, and mechanical overhead stirrer was added 2-hydroxy-4-(methylthio)butanoic acid (130 g, 870 mmol, obtained by stirring Alimet over activated charcoal, filtering and concentrating in a rotovap), 1-octadecanol (351.2 g, 1.30 mol), sodium hydrogen sulfate (2.10 g, 17 mmol), and toluene (1000 mL). The reaction was heated to reflux with removal of water (21.5 mL) during the course of about 4 hours. The reaction was cooled to room temperature overnight and the mixture was filtered. The filtrate was washed with saturated $NaHCO_3$ (1×500 mL), DI water (1×500 mL) and brine (1×500 mL), dried over sodium sulfate, filtered and evaporated to give light brown semi-solid (319.4 g). The semi-solid was treated with hexanes (750 mL) and the resulting mixture was filtered. The solid was washed with hexanes (250 mL) and the combined filtrate was evaporated to give an oil which solidified upon standing (278.8 g). The solid was purified by kugelrohr at 175° C. and 0.1 mm Hg vacuum to give a waxy solid remaining in the distillation pot (214.0 g, 61%). m/z 425 ($MNa^+$).

Step 2: Synthesis of octadecyl 2-hydroxy-4-(methylsulfinyl) butanoate. To a solution of octadecyl 2-hydroxy-4-(methylthio)butanoate (7.18 g, 17.8 mmol) in dichloromethane (160 mL) at 0° C. was added mCPBA (77%, 4.00 g, 17.8 mmol) portionwise over 30 min. The resulting mixture was allowed to warm to room temperature with stirring over the weekend. The reaction was washed with saturated sodium bicarbonate (3×100 mL), 1N HCl (1×100 mL), and brine (1×100 mL). The organic layer was dried over magnesium sulfate, filtered and evaporated to give a crude solid. The solid was purified by silica gel chromatography on a 160 g column with 0-5% methanol/dichloromethane. The desired fractions were collected and evaporated to give a white solid (3.36 g, 45%). $^1$H NMR (500 MHz, DMSO-$d_6$) δ ppm 0.85 (s, 3 H) 1.15-1.33 (m, 30 H) 1.52-1.62 (m, 2 H) 1.80-1.92 (m, 1 H) 1.97-2.06 (m, 1 H) 2.52 (d, J=3.81 Hz, 3 H) 2.61-2.75 (m, 1 H) 2.75-2.89 (m, 1 H) 4.00-4.11 (m, 2 H) 4.11-4.19 (m, 1 H) 5.57-5.65 (m, 1 H). m/z 419 ($MH^+$).

Example 6

Preparation of 2-Hydroxy-4-(Methylsulfinyl)-N-Octylbutanamide

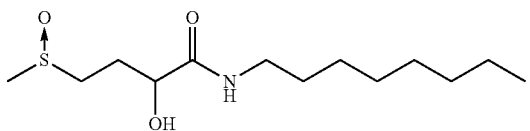 [SMILES: CCCCCCCCNC(=O)C(O)CCS(C)=O]

Step 1: Synthesis of 2-acetoxy-4-(methylthio)butanoic acid. To a solution of 2-hydroxy-4-(methylthio)butanoic acid (50.74 g, 337.8 mmol, obtained by stirring Alimet over activated charcoal, filtering and concentrating in a rotovap) in dichloromethane (1 L) was added triethylamine (93 mL, 667.3 mmol) and the resulting mixture was cooled to 0° C. To the cooled mixture was added acetyl chloride (26 mL, 365.6 mmol) dropwise. The ice bath was removed and the reaction was allowed to warm to room temperature overnight. The reaction was washed with 1N HCl (2×300 mL), and brine (1×300 mL), dried over magnesium sulfate, filtered and evaporated to give an amber oil (59.82 g, 63.1%). m/z 193 ($MH^+$).

Step 2: Synthesis of 4-(methylthio)-1-(octylamino)-1-oxobutan-2-yl acetate. To a solution of 2-acetoxy-4-(methylthio)butanoic acid (6.10 g, 31.7 mmol) in dichloromethane (100 mL) at 0° C. was added thionyl chloride (11.53 mL, 158.5 mmol) slowly over 30 min. The reaction was allowed to warm to room temperature with stirring overnight. The solvent was evaporated and the resulting oil was dried on the high vacuum for 3 hrs. To a solution of the resulting oil in dichloromethane (100 mL) at 0° C. was added triethylamine (8.84 mL, 63.4 mmol) and then octylamine (5.24 mL, 31.7 mmol) and the reaction was allowed to warm to room temperature with stirring overnight. The reaction was evaporated, redissolved in EtOAc (150 mL) and washed with 1N HCl (3×100 mL), saturated sodium bicarbonate (3×100 mL), and brine (1×100 mL). The organic layer was dried over magnesium sulfate, filtered and evaporated to give an oil. The oil was purified by silica gel chromatography with 0-30% EtOAc/heptane to give a yellow oil. (6.61 g, 69%). m/z 304 ($MH^+$).

Step 3: Synthesis of 4-(methylsulfinyl)-1-(octylamino)-1-oxobutan-2-yl acetate. To a solution of 4-(methylthio)-1-(octylamino)-1-oxobutan-2-yl acetate (6.33 g, 20.86 mmol) in dichloromethane (200 mL) at 0° C. was added mCPBA (77%, 4.67 g, 20.86 mmol). The resulting mixture was allowed to warm to room temperature with stirring overnight. The reaction was washed with saturated sodium bicarbonate (3×100 mL), 1N HCl (1×100 mL), and brine (1×100 mL). The organic layer was dried over magnesium sulfate, filtered and evaporated to give a yellow oil (6.7 g, 100%). m/z 320 ($MH^+$).

Step 4: Synthesis of 2-hydroxy-4-(methylsulfinyl)-N-octylbutanamide. To a solution of 4-(methylsulfinyl)-1-(octylamino)-1-oxobutan-2-yl acetate (5.7 g, 17.87 mmol) in methanol (75 mL) was added 1M NaOH (26.8 mL, 26.8 mmol) and the resulting solution was stirred overnight. The reaction was evaporated to a small volume and treated with EtOAc (100 mL) and 1N HCl (100 mL). The layers were separated and the organic layer was dried over magnesium sulfate, filtered and evaporated. The crude material was purified by silica gel chromatography with 0-5% methanol/dichloromethane. The desired fractions were collected and evaporated to give a white solid (3.23 g, 65%). $^1$H NMR (500 MHz, DMSO-$d_6$) δ ppm 0.85 (t, J=6.83 Hz, 3 H) 1.24 (br. s., 10 H) 1.33-1.47 (m, 2 H) 1.73-1.89 (m, 1 H) 1.95-2.10 (m, 1 H) 2.51 (d, J=0.64 Hz, 3 H) 2.58-2.87 (m, 2 H) 2.99-3.14 (m, 2 H) 3.95 (dd, J=7.15, 4.29 Hz, 1 H) 5.69 (d, J=5.09 Hz, 1 H) 7.76 (t, J=5.40 Hz, 1 H). m/z 278 ($MH^+$).

Example 7

Preparation of N-Decyl-2-Hydroxy-4-(Methylsulfinyl)butanamide

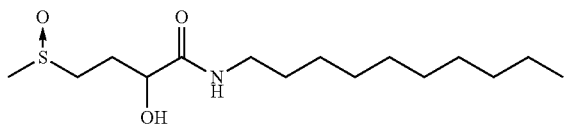 [SMILES: CCCCCCCCCCNC(=O)C(O)CCS(C)=O]

Step 1: Synthesis of 1-(decylamino)-4-(methylthio)-1-oxobutan-2-yl acetate. To a solution of 2-acetoxy-4-(methylthio)butanoic acid (17.1 g, 89 mmol) in dichloromethane (350 mL) at 0° C. was added thionyl chloride (32.4 mL, 445 mmol) dropwise over 1 hr. The reaction was stirred at 0° C. for 1.5 hrs then the cooling bath was removed and the reaction was warmed to room temperature with stirring for 3 hrs. The solvent was evaporated and the resulting oil was dried under high vacuum for 1 hr to give an orange oil. A solution of the resulting oil in dichloromethane (~30 mL) was added to a solution of triethylamine (24.8 mL, 178 mmol) and decylamine (17.8 mL, 89 mmol) in dichloromethane (150 mL) at 0° C. and the reaction was allowed to warm to room temperature with stirring overnight. The reaction was evaporated, redissolved in EtOAc (300 mL) and washed with 1N HCl (3×150 mL), saturated sodium bicarbonate (3×150 mL), and brine(1×150 mL). The organic layer was dried over magnesium sulfate, filtered and evaporated to give an oil. The oil was purified by silica gel chromatography with 0-40% EtOAc/heptane to give a yellow oil. (21.1 g, 71%). m/z 332 (MH$^+$).

Step 2: Synthesis of 1-(decylamino)-4-(methylsulfinyl)-1-oxobutan-2-yl acetate. To a solution of 1-(decylamino)-4-(methylthio)-1-oxobutan-2-yl acetate (21.1 g, 63.4 mmol) in methanol (110 mL) at 0° C. was added hydrogen peroxide (30%, 19.43 mL, 190 mmol) and the ice bath was removed. The reaction was allowed to stir for 5.5 hr. The reaction was diluted with water (400 mL) and then extracted with EtOAc (200 mL) to give an emulsion which did not separate after 18 hrs. The emulsion was treated with brine (250 mL) and the layers separated. The aqueous layer was extracted with EtOAc (200 mL) and the combined organic layers were washed with 10% sodium bisulfite. The organic layer was dried over magnesium sulfate, filtered and evaporated to give an orange oil (22.4 g, 100%). m/z 348 (MH$^+$).

Step 3: Synthesis of N-decyl-2-hydroxy-4-(methylsulfinyl)butanamide. To a solution of 1-(decylamino)-4-(methylsulfinyl)-1-oxobutan-2-yl acetate (22.4 g, 63.4 mmol) in methanol (300 mL) was added 2.5 N NaOH (39 mL, 97.5 mmol) and the resulting solution was stirred at room temperature for 5 hrs. The reaction was quenched with concentrated HCl (12.5 mL) and then evaporated to a small volume. The resulting mixture was treated with EtOAc (200 mL) and then washed with 1N HCl (150 mL), saturated sodium bicarbonate (50 mL), dried over magnesium sulfate, filtered and evaporated to give a solid. The solid was dissolved in dichloromethane and purified by silica gel chromatography with 0-10% methanol/dichloromethane. The desired fractions were collected and evaporated to give a white solid (13.6 g, 70%). $^1$H NMR (500 MHz, DMSO-d$_6$) δ ppm 0.85 (t, J=6.83 Hz, 3 H) 1.15-1.32 (m, 14 H) 1.32-1.46 (m, 2 H) 1.75-1.87 (m, 1 H) 1.94-2.06 (m, 1 H) 2.51 (d, J=1.27 Hz, 3 H) 2.58-2.88 (m, 2 H) 3.00-3.12 (m, 2 H) 3.89-4.02 (m, 1 H) 5.69 (d, J=5.40 Hz, 1 H) 7.76 (t, J=5.56 Hz, 1 H). m/z 306 (MH$^+$).

Example 8

Preparation of
N-Dodecyl-2-Hydroxy-4-(Methylsulfinyl)butanamide

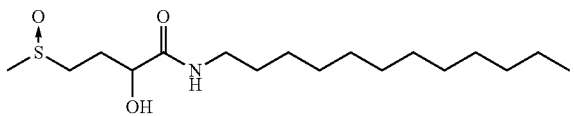 [SMILES: CCCCCCCCCCCCNC(=O)C(O)CCS(C)=O]

Step 1: Synthesis of 1-(dodecylamino)-4-(methylthio)-1-oxobutan-2-yl acetate. To a solution of 2-acetoxy-4-(methylthio)butanoic acid (17.1 g, 89 mmol) in dichloromethane (350 mL) at 0° C. was added thionyl chloride (32.4 mL, 445 mmol) dropwise over 1 hr. The reaction was stirred at 0° C. for 1.5 hrs then the cooling bath was removed and the reaction was warmed to room temperature with stirring for 3 hrs. The solvent was evaporated and the resulting oil was dried under high vacuum for 1 hr to give an orange oil. A solution of the resulting oil in dichloromethane (~30 mL) was added to a solution of triethylamine (24.8 mL, 178 mmol) and dodecylamine (20.5 mL, 89 mmol) in dichloromethane (150 mL) at 0° C. and the reaction was allowed to warm to room temperature with stirring overnight. The reaction was evaporated, re-dissolved in EtOAc (300 mL) and washed with 1N HCl (3×150 mL), saturated sodium bicarbonate (3×150 mL), and brine (1×150 mL). The organic layer was dried over magnesium sulfate, filtered and evaporated to give an oil. The oil was purified by silica gel chromatography with 0-40% EtOAc/heptane to give a yellow oil. (22.5 g, 70%). m/z 360 (MH$^+$).

Step 2: Synthesis of 1-(dodecylamino)-4-(methylsulfinyl)-1-oxobutan-2-yl acetate. To a solution of 1-(dodecylamino)-4-(methylthio)-1-oxobutan-2-yl acetate (22.5 g, 62.6 mmol) in methanol (110 mL) at 0° C. (a precipitate formed) was added hydrogen peroxide (30%, 19.19 mL, 188 mmol) and the ice bath was removed and everything dissolved. The reaction was allowed to stir for 5.5 hr. The reaction was diluted with water (400 mL) and then extracted with EtOAc (200 mL) to give an emulsion which did not separate after 18 hrs. The emulsion was treated with brine (250 mL) and the layers separated. The aqueous layer was extracted with EtOAc (200 mL) and the combined organic layers were washed with 10% sodium bisulfite. The organic layer was dried over magnesium sulfate, filtered and evaporated to give an orange oil (25.0 g, 100%). m/z 376 (MH$^+$).

Step 3: Synthesis of N-dodecyl-2-hydroxy-4-(methylsulfinyl)butanamide. To a solution of 1-(dodecylamino)-4-(methylsulfinyl)-1-oxobutan-2-yl acetate (25 g, 62.6 mmol) in methanol (350 mL) was added 2.5 N NaOH (40 mL, 100 mmol) and the resulting solution was stirred at room temperature for 5 hrs. The reaction was quenched with concentrated HCL (12.5 mL) and then evaporated to a small volume. The resulting mixture was treated with EtOAc (200 mL) and then washed with 1N HCl (150 mL), saturated sodium bicarbonate (50 mL), dried over magnesium sulfate, filtered and evaporated to give a solid. The solid was dissolved in dichloromethane and purified by silica gel chromatography with 0-10% methanol/dichloromethane. The desired fractions were collected and evaporated to give a white solid (16.7 g, 80%). $^1$H NMR (500 MHz, DMSO-d$_6$) δ ppm 0.85 (t, J=6.83 Hz, 3 H) 1.15-1.33 (m, 18 H) 1.33-1.46 (m, 2 H) 1.72-1.87 (m, 1 H) 1.92-2.09 (m, 1 H) 2.51 (d, J=1.27 Hz, 3 H) 2.56-2.87 (m, 2 H) 3.00-3.12 (m, 2 H) 3.90-4.00 (m, 1 H) 5.69 (d, J=5.40 Hz, 1 H) 7.71-7.82 (m, 1 H). m/z 334 (MH$^+$).

Example 9

Preparation of
2-Amino-4-(Methylsulfinyl)-N-Octylbutanamide

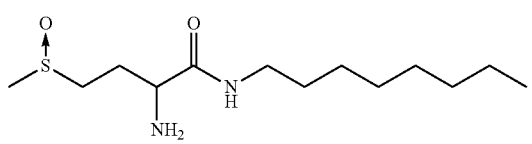 [SMILES: CCCCCCCCNC(=O)C(N)CCS(C)=O]

Step 1: Synthesis of tert-butyl (4-(methylsulfinyl)-1-(octylamino)-1-oxobutan-2-yl)carbamate. To a mixture of 2-((tert-butoxycarbonyl)amino)-4-(methylsulfinyl)butanoic acid (10.0 g, 37.7 mmol) and HOBt (6.35 g, 41.5 mmol) in dichloromethane (200 mL) at 0° C. was added triethylamine (10.5 mL, 75.4 mmol) and EDAC (7.95 g, 41.5 mmol). After stirring for 20 minutes octylamine was added and the solution was allowed to warm to room temperature and stirred for 3 days. The reaction was washed with saturated sodium bicarbonate (2×100 mL), 1N HCl (2×100 mL), and brine (1×100 mL). The organic layer was dried over magnesium sulfate, filtered and evaporated to give an oil which solidified upon standing. The solid was purified by silica gel chromatography with 0-5% methanol/dichloromethane to give a white solid (13.1 g, 92%). m/z 377 (MH$^+$).

Step 2: Synthesis of 2-amino-4-(methylsulfinyl)-N-octylbutanamide. To a solution of tert-butyl (4-(methylsulfinyl)-1-(octylamino)-1-oxobutan-2-yl)carbamate (6.43 g, 17.1 mmol) in dichloromethane (65 mL) at 0° C. was added TFA (65 mL) and the ice bath was removed. After stirring for 1 hour the reaction was concentrated to give an oil. The oil was purified by silica gel chromatography with 0-10% methanol/dichloromethane (with 15% ammonium hydroxide additive in methanol) to give a white solid (4.5 g, 95%). $^1$H NMR (500 MHz, DMSO-d$_6$) δ ppm 0.87 (t, J=6.83 Hz, 3 H) 1.19-1.33 (m, 10 H) 1.36-1.47 (m, 2 H) 1.61-1.78 (m, 1 H) 1.84-1.99 (m, 1 H) 2.17-2.38 (m, 1 H) 2.52 (s, 3 H) 2.61-2.72 (m, 1 H) 2.75-2.84 (m, 1 H) 2.99-3.13 (m, 2 H) 3.19-3.29 (m, 1 H) 3.28-3.46 (m, 1 H) 7.89 (br. s., 1 H). m/z 277 (MH$^+$).

Example 10

Properties of Sulfoxide-Based Compounds or Mixtures Thereof

To determine whether the sulfoxide-based compounds synthesized in Examples 1-9 had surfactant properties, the critical micelle concentration (CMC), surface tension, and solubility were determined. The Wilhelmy plate method was used to determine the equilibrium surface or interfacial tension at an air-liquid interface. A Cahn DCA 322 high-sensitivity balance was used to perform the measurement. Glass slides manufactured by Corning with a width of 22 mm and thickness of 0.1 mm were used as probes; the motor speed was set to be 160 µm/sec. The slides were slowly lowered perpendicular to the interface of the test solution (at 25° C. and atmospheric pressure) and the force exerted on the plate due to wetting was measured. The measured force was converted to surface tension using the Wilhelmy equation. The CMC was calculated according to standard procedures. The solubility was calculated in water at 25° C. and atmospheric pressure.

The following compounds were tested: (1) hexyl 2-hydroxy-4-(methylthio)butanoate (R6SO); (2) octyl 2-hydroxy-4-(methylsulfinyl)butanoate (R8SO); (3) a mixture of 70 wt % R8SO and 30 wt % decyl 2-hydroxy-4-(methylsulfinyl)butanoate (R10SO); (4) a mixture of 70 wt % R8SO and 30 wt % dodecyl 2-hydroxy-4-(methylsulfinyl)butanoate (R12SO); (5) 2-hydroxy-4-(methylsulfinyl)-N-octylbutanamide (R8NHSO); (6) a mixture of 60 wt % R8NHSO and 40 wt % 2-hydroxy-4-(methylsulfinyl)-N-decylbutanamide (R10NHSO); (7) a mixture of 75 wt % R8NHSO and 25 wt % 2-hydroxy-4-(methylsulfinyl)-N-dodecylbutanamide (R12NHSO); as well as the commercially available nonionic surfactants (8) Igepal® CO-630, a branched nonylphenol ethoxylate, and two alkyl ethylene oxides, (9) hexaethylene glycol monododecyl ether (C12E6) and (10) hexaethylene glycol monodecyl ether (C10E6). Table 1 presents the CMC and surface tension of each compound or mixture of compounds, as well as the solubility of the sulfoxide-based compounds (in water at 25° C. and atmospheric pressure).

TABLE 1

CMC and Surface Tension

| # | Compound | CMC (mM) | Surface Tension (mN/m) at CMC | Solubility (wt/wt total) |
|---|---|---|---|---|
| 1 | R6SO | 120.9 | 33 | >50% |
| 2 | R8SO | 11.7 | 29 | >50% |
| 3 | R8SO/R10SO (70:30) | 1.26 | 28 | >50% |
| 4 | R8SO/R12SO (70:30) | 0.3 | 27 | >50% |
| 5 | R8NHSO | 10.3 | 29 | >50% |
| 6 | R8NHSO/R10NHSO (60:40) | 2.9 | 28 | >50% |
| 7 | R8NHSO/R12NHSO (75:25) | 0.4 | 30 | >50% |
| 8 | Igepal ® CO-630 | 0.08 | 31 | |
| 9 | C12E6 | 0.087 | 41 | |
| 10 | C10E6 | 0.90 | 42 | |

Example 11

Wetting Ability of Sulfoxide-Based Compounds

The Draves Wetting Test was used to assess the wetting ability of the sulfoxide-based compounds. This test determines the ability of a surfactant solution to displace air from a weighted cotton skein. Four different concentrations of the sulfoxide-based compounds, and Igepal® CO-630 were tested. The Draves wetting test was run according to ASTM D2281-68. That is, 500 ml of surfactant solution was poured into a 500 ml graduated cylinder (38 cm in height), and 5.0 g of a standard skein hooked with a lead anchor was dropped into the solution. Initially the skein floated in the solution, after wetting, the skein would sink. The time between dropping the skein into the solution and its sinking was recorded and termed the wetting time. Table 2 presents the results.

TABLE 2

Draves Wetting Test

| Compound | Concentration | Time for skein to sink |
|---|---|---|
| R6SO | 0.50% | ~6 hr |
| | 0.25% | >24 hr |
| | 0.10% | >24 hr |
| | 0.05% | >24 hr |
| R8SO | 0.50% | <5 sec |
| | 0.25% | 5 sec |
| | 0.10% | >30 min |
| | 0.05% | >30 min |
| R8SO/R10SO (70:30) | 0.50% | 3 sec |
| | 0.25% | 5 sec |
| | 0.10% | 8 sec |
| | 0.05% | >5 min |
| R8SO/R12SO (70:30) | 0.50% | 12 sec |
| | 0.25% | 21 sec |
| | 0.10% | 55 sec |
| | 0.05% | >5 min |
| Igepal ® CO-630 | 0.50% | <5 sec |
| | 0.25% | 7 sec |
| | 0.10% | 12 sec |
| | 0.05% | 30 sec |

Example 12

Laundry Test

Laundry formulations were formulated that comprised 10 wt % of a nonionic surfactant (e.g., sulfoxide-based compound, Igepal, etc.), 10 wt % of an anionic surfactant (e.g., SDBS), 0.2 wt % of sodium methyl cocoyl taurate, 0.2 wt % sodium diethylenetriamine penta(methylene phosphoric acid), 5 wt % sodium citrate, 0.8 wt % sodium chloride, 2 wt % sodium hydroxide, 0.3 wt % boric acid, 3% wt % propylene glycol, 0.1 wt % fluorescer, 0.4 wt % protease, 0.15 wt % mannose, 0.4 wt % amylase, 0.2 wt % polyvinylpyrroldinone, 0.2 wt % polyvinylpyridine oxide, with water to balance.

The laundry formulations were tested on a series of different types of stains on cotton swatches and polyester-cotton (PE/C) swatches. Fabrics were purchased from Testfabrics Inc. The laundry formulation presented above was diluted to a 3 g in 1 L tap water ratio and run through a 20 min wash +5 min rinse cycle at 30° C. Reflectance was measured at a wavelength of 460 nm using an optoelectric colorimeter using a modification of testing procedure D4265-98 (Reapproved 2007). The changes in reflectance are presented in Table 4. A positive value indicates better cleaning efficiency as opposed to the control which was made with Igepal® CO 630 as the nonionic. On the average, the formulation comprising the sulfoxide-based surfactants had no changes in reflectance relative to the control formulation.

TABLE 3

Change in Reflectance normalized to control formulation with Igepal ® CO 630 as the nonionic surfactant

| Type of Stain | Test Formulation 70:30 R8SO/R12SO mixture as the nonionic surfactant instead of Igepal ® CO 630 |
|---|---|
| Blood/milk/ink on cotton | −3.5% ± 5.0% |
| Tea on cotton | −7.1% ± 33.3% |
| Coffee on cotton | 38.5% ± 6.1% |
| Grass on cotton | 4.8% ± 11.3% |
| Wine on cotton | 2.7% ± 3.3% |
| Lipstick on cotton | 4.4% ± 16.5% |
| Chocolate drink on cotton | 46.6% ± 0.0% |
| Blood/milk/ink on PE/C | −29.1% ± 3.5% |
| Tea on PE/C | −17.6% ± 23.5% |
| Coffee on PE/C | −5.7% ± 16.7% |
| Grass on PE/C | 3.0% ± 7.1% |
| Wine on PE/C | −5.6% ± 3.1% |
| Lipstick on PE/C | −25.0% ± 5.6% |
| Chocolate drink on PE/C | 1.3% ± 5.1% |
| Average | 0.5% ± 12.9% |

Example 13

Toxicology Studies

The potential hazards of the sulfoxide-based compounds were examined by evaluating the toxicity of R8SO in three standard bioassays (i.e., fresh water algae growth inhibition test, *Daphnia* acute immobilization test, and fresh water fish acute toxicity test).

The fresh water algae growth inhibition test was conducted according to OECD 201 guidelines. Briefly, exponentially growing fresh water algae were exposed to several concentrations of the test substances in batch cultures over a period of 72 hours. The cultures were allowed unrestricted exponential growth under nutrient sufficient conditions and continuous fluorescent illumination. Three replicates at each test concentration were used. Growth was monitored over time and compared to the average growth of control cultures (with no test substances). Growth and growth inhibition are quantified from measurements of the algal biomass as a function of time. These data were used to calculate EC50, which is the concentration of the test substance that results in a 50 percent reduction in growth relative to the control. R8SO had an EC50 of 175 ppm at 72 hr.

The *Daphnia* acute immobilization test was performed according to the OECD 202 guidelines. Briefly, young daphnids, ages less than 24 hours at the start of the test, were exposed to the test substances at a range of concentrations for a period of 48 hours. Generally, at least 20 animals, preferably divided into four groups of five animals each, were tested for each test concentration and for the controls (i.e., no test substance). The *Daphnia* were not fed during the test. At least 2 mL of test solution were provided for each animal. Temperatures were held between 18 and 22° C., and for each single test the temperature was within ±1° C. Immobilization was recorded at 24 hours and 48 hours, and compared to control values. Those animals that could not swim within 15 seconds after gentle agitation of the test container were considered to be immobile. The results are used to calculate the EC50 (the concentration at which 50% of the animals were immobilized) at 48 hours. The EC50 of R8SO at 48 hr was 79 ppm.

The fresh water fish acute toxicity test was conduced according to OECD 203 guidelines. For this test, fresh water fish (i.e., fathead minnows) were exposed to a series of concentrations of the test substances for a period of 96 hours. At least seven fishes were used at each test concentration and in the controls. Mortalities were recorded at 24, 48, 72, and 96 hours. Fish were considered dead if there was no visible movement (e.g. gill movements) and if touching of the caudal peduncle produced no reaction. The mortality counts were used to determine LC50, the concentration that killed 50% of the fish. R8SO had a LC50 of 148 ppm at 96 hr.

Example 14

Preparation of Dodecyl 2-((2-Hydroxy-4-(Methylsulfinyl)butanoyl)oxy)-4-(Methylsulfinyl)butanoate

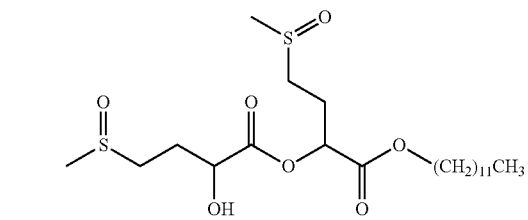

Step 1—Synthesis of dodecyl 2-((2-hydroxy-4-(methylthio)butanoyl)oxy)-4-(methylthio)butanoate. To 2-hydroxy-4-(methylthio)butanoic acid (HMTBa; Alimet 88%) (10.0 g, 58.6 mmol) was added 1-dodecanol (6.55 g, 35.2 mmol), p-toluenesulfonic acid (0.56 g, 2.9 mmol) in toluene (50 mL) in a round bottom flask that was fitted with a Dean Stark trap and reflux condenser. The resulting mixture was heated to reflux with removal of water overnight. The reaction was cooled to room temperature and then diluted with ethyl acetate (65 mL) and washed with sat. NaHCO$_3$ (3×30 ml), water (1×30 ml), dried over magnesium sulfate, filtered and evaporated. The crude product was purified by silica gel chromatography with 0-30% EA/Heptane to give an oil (1.91 g, 7.2%). m/z 451 (MH$^+$).

Step 2—Synthesis of dodecyl 2-((2-hydroxy-4-(methylsulfinyl)butanoyl)oxy)-4-(methylsulfinyl)butanoate. To a solution of dodecyl 2-((2-hydroxy-4-(methylthio)butanoyl)oxy)-4-(methylthio)butanoate (1.81 g, 4.0 mmol) in methanol (25 ml) at 0° C. was slowly added hydrogen peroxide (30%, 1.3 ml, 12.7 mmol). The reaction was stirred for 30 min and then the ice bath was removed and stirring continued overnight. The reaction was diluted with ethyl acetate (350 mL) and washed with water (1×100 mL) and 10% sodium bisulfite (1×100 ml), dried over magnesium sulfate, filtered and evaporated to give a light yellow oil. The oil was purified by silica gel chromatography with 0-10% MeOH/DCM to give an oil (0.68 g, 35%). m/z 483 (MH$^+$).

Example 15

Preparation Oligomeric Mixture Obtained from Oxidation of the Condensation Products of HMTBa with 1-Octanol and 1-Dodecanol

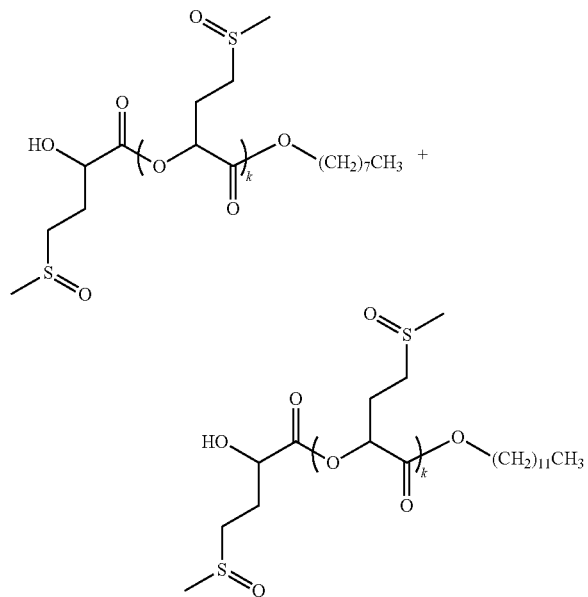

2-Hydroxy-4-(methylthio)butanoic acid (HMTBa; Alimet, 88%) (5.00 g, 29.3 mmol), 1-octanol (2.52 g, 19.4 mmol), 1-dodecanol (1.31 g, 7.0 mmol), and Amberlyst-15 (0.5 g) were mixed together and heated at 110° C. Nitrogen was bubbled through the mixture to help carry away the water. Analysis indicated the reaction was completed within 2 hours. The mixture was cooled to 25° C. and diluted with 15 mL of ethyl acetate. The mixture was filtered and the resin was washed with ethyl acetate (10 mL). The combined filtrate was cooled to 5° C. and the hydrogen peroxide was added (the reaction was mildly exothermic). After one hour, the mixture was warmed to 25° C. and stirred until reaction completion. The mixture started out as two phases and as the reaction progressed the mixture became homogeneous. Analysis indicated the oxidation was completed between 4 and 20 hours. The mixture was washed with water (1×15 mL), aqueous 10% sodium bisulfite (1×15 mL, the wash was mildly exothermic), aqueous 1.0 M sodium bicarbonate (1×15 mL) and water (2×15 mL). The organic phase was evaporated at 50° C. and reduced pressure using a rotary evaporator to give a mixture of the monomer, dimer, trimer and oligomers of both octyl and dodecyl esters as a light-yellow, viscous liquid (7.12 g, 87%). k=0 C8, m/z 279 (MH$^+$), k=1 C8, m/z 427 (MH$^+$), k=2 C8, m/z 575 (MH$^+$), k=0 C12, m/z 335 (MH$^+$), k=1 C12, m/z 483 (MH$^+$), k=2 C12, m/z 631 (MH$^+$).

The resultant mixture of R8SO monomers, dimers, trimers, and other oligomers and R12SO monomers, dimers, trimers, and other oligomers had a lower CMC than a mixture of R8SO monomers and R12SO monomers. The CMC of the mixture of R8SO and R12SO monomers and oligomers was 0.043 mM, whereas the mixture of R8SO and R12SO momomers had a CMC of 0.3 mM (see Table 1, Example 10).

Example 16

Preparation of Oligomeric Mixture Obtained from Oxidation of the Condensation Products of HMTBa and NEODOL-9

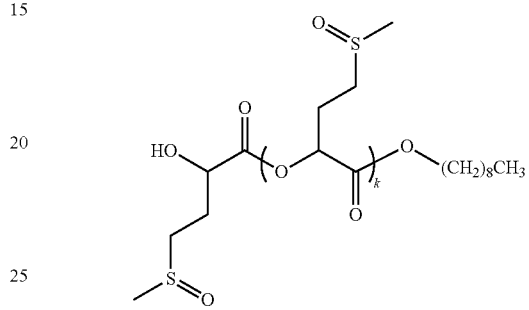

To 2-hydroxy-4-(methylthio)butanoic acid (Alimet, 88%) (5.09 g, 29.8 mmol) in a 20 ml vial was added NEODOL-9 (3.4 g, 23.5 mmol) and Amberlyst 15 (0.53 g). The resulting mixture was heated at 110° C. while bubbling a stream of nitrogen through it for 2 hrs. The reaction was cooled to room temperature, diluted with ethyl acetate (25 mL) and then filtered. The filtrate was cooled on an ice bath and then treated with hydrogen peroxide (30%, 6.1 ml, 59.6 mmol). The reaction was stirred for 30 min and then the ice bath was removed and stirring continued overnight at room temperature. The reaction was washed with 30 mL water plus 10 mL of brine, 10% sodium bisulfite (1×40 ml), sat. sodium bicarbonate (2×40 mL) and then water (2×20 mL). The organic layer was separated and evaporated to give the monomer, dimer and oligomer mixture as a light yellow oil (6.43 g, 82%). k=0, m/z 293 (MH$^+$), k=1, m/z 441 (MH$^+$), k=2, m/z 589 (MH$^+$), k=0 C10, m/z 307 (MH$^+$), k=0 C11, m/z 321 (MH$^+$).

Example 17

Preparation of Oligomeric Mixture Obtained from Oxidation of the Condensation Products of HMTBa and 1-Decanol

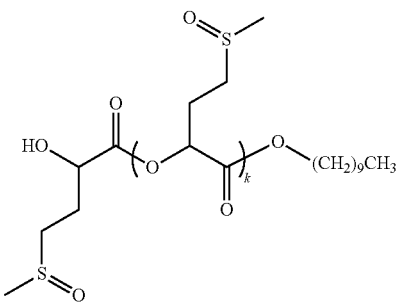

To 2-hydroxy-4-(methylthio)butanoic acid (Alimet 88%) (5.14 g, 30.1 mmol) in a 20 ml vial was added 1-decanol (4.27 g, 26.98 mmol) and Amberlyst 15 (0.52 g). The resulting mixture was heated at 110° C. while bubbling a stream of nitrogen through it for 2 hrs. The reaction was cooled to room temperature, diluted with ethyl acetate (25 mL) and then filtered. The filtrate was cooled on an ice bath and then treated with hydrogen peroxide (30%, 4.6 ml, 45 mmol). The reaction was allowed to warm to room temperature with stirring overnight. The reaction was washed with water (1×40 mL), 10% sodium bisulfite (1×40 ml), sat. sodium bicarbonate (2×40 mL) and then water (2×20 mL, emulsion formed on second wash which separated after several days). The organic layer was dried over magnesium sulfate and then filtered. The filtrate was decanted to remove a precipitate and evaporated to give the monomer, dimer, trimer and oligomer mixture as a light yellow oil (7.9 g, 91%). k=0, m/z 307 (MH$^+$), k=1, m/z 455 (MH$^+$), k=2, m/z 603 (MH$^+$).

Example 18

Preparation of 4-(Methylsulfinyl)-1-Oxo-1-(Tetradecyloxy)butan-2-yl 2-Hydroxy-4-(Methylsulfinyl)butanoate

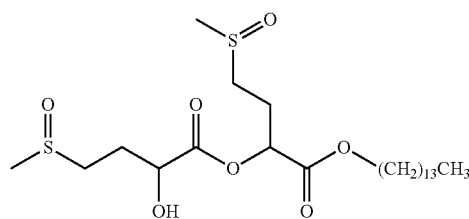

Step 1-4-(methylthio)-1-oxo-1-(tetradecyloxy)butan-2-yl 2-hydroxy-4-(methylthio)butanoate. To 2-hydroxy-4-(methylthio)butanoic acid (Alimet 88%) (10.1 g, 59.2 mmol) was added 1-tetradecanol (7.57 g, 35.3 mmol), p-toluenesulfonic acid (0.55 g, 2.9 mmol) in toluene (50 mL) in a round bottom flask that was fitted with a Dean Stark trap and reflux condenser. The resulting mixture was heated to reflux with removal of water overnight. The reaction was cooled to room temperature and then diluted with ethyl acetate (65 mL) and washed with sat. NaHCO$_3$ (3×30 mL), water (1×30 mL), dried over magnesium sulfate, filtered and evaporated to give a dark oil. The oil was purified by silica gel chromatography with 0-30% ethyl acetate/heptane to give a light yellow oil (3.34 g, 24%). $^1$H NMR (500 MHz, DMSO-d$_6$) δ ppm 0.85 (t, J=6.83 Hz, 3 H) 1.11-1.38 (m, 22 H) 1.56 (t, J=6.20 Hz, 2 H) 1.76-1.99 (m, 2 H) 1.99-2.10 (m, 8 H) 2.51-2.64 (m, 4 H) 3.99-4.15 (m, 2 H) 4.16-4.32 (m, 1 H) 5.00-5.16 (m, 1 H) 5.51-5.69 (m, 1 H).

Step 2-4-(methylsulfinyl)-1-oxo-1-(tetradecyloxy)butan-2-yl 2-hydroxy-4-(methylsulfinyl)butanoate. To a solution of 4-(methylthio)-1-oxo-1-(tetradecyloxy)butan-2-yl 2-hydroxy-4-(methylthio)butanoate (3.24 g, 6.77 mmol) in ethyl acetate (25 ml) at 0° C. was added hydrogen peroxide (30%, 2.07 ml, 20.3 mmol). The reaction was stirred for 30 min and then the ice bath was removed and stirring continued over three days. The reaction was diluted with ethyl acetate (50 mL) and washed with 10% sodium bisulfite (1×30 mL), dried over magnesium sulfate, filtered and evaporated to give a light yellow oil. The oil was purified by silica gel chromatography with 0-10% MeOH/DCM to give a viscous oil (1.83 g, 53%). m/z 511 (MH$^+$).

Example 19

Preparation of Hexadecyl 2-((2-Hydroxy-4-(Methylsulfinyl)butanoyl)oxy)-4-(Methylsulfinyl)butanoate

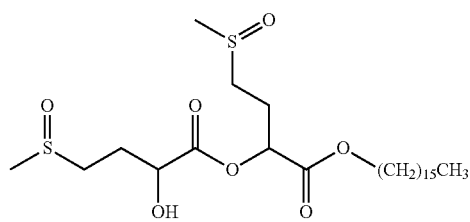

Step 1-hexadecyl 2-((2-hydroxy-4-(methylthio)butanoyl)oxy)-4-(methylthio)butanoate. To 2-hydroxy-4-(methylthio)butanoic acid (Alimet 88%) (10.0 g, 58.6 mmol) was added 1-hexadecanol (8.55 g, 35.3 mmol), p-toluenesulfonic acid (0.56 g, 2.9 mmol) in toluene (50 mL) in a round bottom flask that was fitted with a Dean Stark trap and reflux condenser. The resulting mixture was heated to reflux with removal of water overnight. The reaction was cooled to room temperature and then diluted with ethyl acetate (65 mL) and washed with sat. NaHCO$_3$ (3×30 mL), water (1×30 mL), dried over magnesium sulfate, filtered and evaporated to give a dark brown oil. The oil was purified by silica gel chromatography with 0-30% ethyl acetate/heptane to give a light yellow oil (3.2 g, 22%). $^1$H NMR (500 MHz, DMSO-d$_6$) δ ppm 0.85 (t, J=6.68 Hz, 3 H) 1.10-1.35 (m, 26 H) 1.48-1.64 (m, 2 H) 1.76-1.98 (m, 2 H) 1.99-2.12 (m, 8 H) 2.50-2.66 (m, 4 H) 4.01-4.18 (m, 2 H) 4.17-4.32 (m, 1 H) 5.00-5.15 (m, 1 H) 5.54-5.72 (m, 1 H).

Step 2-2-((2-hydroxy-4-(methylsulfinyl)butanoyl)oxy)-4-(methylsulfinyl)butanoate. To a solution of hexadecyl 2-((2-hydroxy-4-(methylthio)butanoyl)oxy)-4-(methylthio)butanoate (3.05 g, 6.02 mmol) in ethyl acetate (25 ml) at 0° C. was added hydrogen peroxide (30%, 1.84 ml, 18.05 mmol). The reaction was stirred for 30 min and then the ice bath was removed and stirring continued over three days. The reaction was diluted with ethyl acetate (50 mL) and washed with 10% sodium bisulfite (1×30 mL), dried over magnesium sulfate, filtered and evaporated to give a light yellow oil. The oil was purified by silica gel chromatography with 0-10% MeOH/DCM to give a white waxy solid (2.44 g, 75%). m/z 539 (MH$^+$).

What is claimed is:

1. A compound comprising Formula (I):

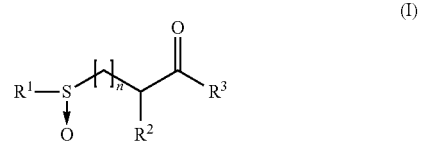

wherein:
R$^1$ is hydrocarbyl or substituted hydrocarbyl;
R$^2$ is OH, OR$^4$, NH$_2$, or NHR$^4$;
R$^3$ is OR$^5$ or NHR$^5$;

$R^4$ is hydrocarbyl or substituted hydrocarbyl;
$R^5$ is hydrocarbyl or substituted hydrocarbyl having six or more carbon atoms in the principal chain; and
n is an integer of 1 or greater;
provided, however, that when n is 1 and $R^2$ is $OR^4$, then $R^4$ comprises other than pyrrolyl or indolyl; when n is 2, $R^2$ is $NH_2$, and $R^3$ is $NHR^5$, then $R^5$ comprises other than aminoacyl, amide, piperidyl, pyridyl, pyrimidyl, or thioester; when n is 2 and $R^2$ is NH-methacryloyl, then $R^3$ is other than NH-menthyl; or when n is 2 and $R^3$ is NH—$C_{14}$ alkyl, then $R^2$ is other than $NH_2$ or NH—$C(O)(CH_2)_{16}CH_3$.

2. The compound of claim 1, wherein $R^1$ is alkyl; $R^4$ is alkyl, acyl, $(CH_2CH_2O)_pH$, $(CH_2CH(CH_3)O)_pH$, or a combination of $(CH_2CH_2O)_pH$ and $(CH_2CH(CH_3)O)_pH$; p is an integer of 2 or greater; and $R^5$ is $C_6$ to $C_{30}$ alkyl.

3. The compound of claim 2, wherein n is 2; $R^1$ is methyl; $R^2$ is $NH_2$ or $NHR^4$; and $R^5$ is $C_6$ to $C_{22}$ alkyl.

4. The compound of claim 1, wherein the compound comprises Formula (Ia):

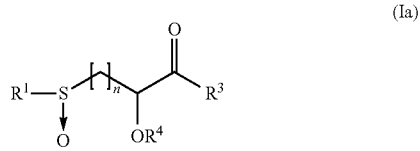

(Ia)

wherein:
$R^1$, $R^3$, and n are as defined above; and
$R^4$ is hydrogen, hydrocarbyl, or substituted hydrocarbyl; provided, however, that when n is 1, then $R^4$ comprises other than pyrrolyl or indolyl.

5. The compound of claim 4, wherein $R^1$ is alkyl; $R^4$ is hydrogen, alkyl, acyl, $(CH_2CH_2O)_pH$, $(CH_2CH(CH_3)O)_pH$, or a combination of $(CH_2CH_2O)_pH$ and $(CH_2CH(CH_3)O)_pH$; p is an integer of 2 or greater; and $R^5$ is $C_6$ to $C_{30}$ alkyl.

6. The compound of claim 5, wherein n is 2; $R^1$ is methyl; and $R^5$ is $C_6$ to $C_{22}$ alkyl.

7. The compound of claim 1, wherein the compound has a critical micelle concentration (CMC) in water at 25° C. and atmospheric pressure.

8. The compound of claim 1, wherein the compound is used in commercial or residential laundry products, industrial or household cleaning products, floor polishing products, personal care or cosmetic products, textile processing, metal processing, paper processing, agricultural applications, latex production, paper de-inking, or crude oil drilling applications.

9. A compound comprising Formula (II):

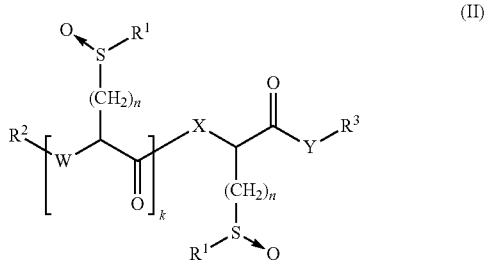

(II)

wherein:
$R^1$ is hydrocarbyl or substituted hydrocarbyl;
$R^2$ is hydrogen, hydrocarbyl, or substituted hydrocarbyl;
$R^3$ is hydrocarbyl or substituted hydrocarbyl having six or more carbon atoms in the principal chain;
W, X, and Y are independently O or NH; and
k and n are independently integers of 1 or greater.

10. The compound of claim 9, wherein $R^1$ is alkyl; $R^2$ is hydrogen, alkyl, acyl, $(CH_2CH_2O)_pH$, $(CH_2CH(CH_3)O)_pH$, or a combination of $(CH_2CH_2O)_pH$ and $(CH_2CH(CH_3)O)_pH$; p is an integer of 2 or greater; and $R^3$ is $C_6$ to $C_{30}$ alkyl.

11. The compound of claim 10, wherein n is 2, k is 1, 2, 3, or 4; $R^1$ is methyl; $R^2$ is hydrogen; $R^3$ is $C_6$ to $C_{22}$ alkyl; and W and X are oxygen.

12. The compound of claim 9, wherein the compound has a critical micelle concentration (CMC) in water at 25° C. and atmospheric pressure.

13. The compound of claim 9, wherein the compound is used in commercial or residential laundry products, industrial or household cleaning products, floor polishing products, personal care or cosmetic products, textile processing, metal processing, paper processing, agricultural applications, latex production, paper de-inking, or crude oil drilling applications.

14. A composition comprising a mixture of compounds comprising Formula (II), the mixture comprising at least two different compounds comprising Formula (II):

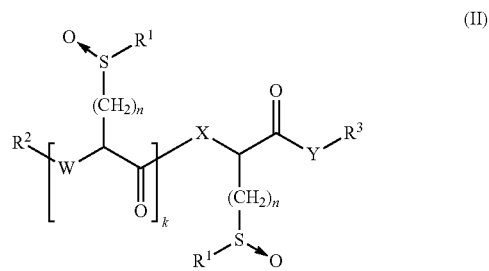

(II)

wherein:
$R^1$ is hydrocarbyl or substituted hydrocarbyl;
$R^2$ is hydrogen, hydrocarbyl, or substituted hydrocarbyl;
$R^3$ is hydrocarbyl or substituted hydrocarbyl having six or more carbon atoms in the principal chain;
W, X, and Y are independently O or NH;
k is an integer of 0 or greater; and
n is an integer of 1 or greater.

15. The composition of claim 14, wherein the mixture comprises compounds in which k is 0, 1, 2, 3, 4, or a combination thereof.

16. The composition of claim 14, wherein $R^1$ is alkyl; $R^2$ is hydrogen, alkyl, acyl, $(CH_2CH_2O)_pH$, $(CH_2CH(CH_3)O)_pH$, or a combination of $(CH_2CH_2O)_pH$ and $(CH_2CH(CH_3)O)_pH$; p is an integer of 2 or greater; and $R^3$ is $C_6$ to $C_{30}$ alkyl.

17. The composition of claim 16, wherein n is 2, $R^1$ is methyl; $R^2$ is hydrogen; and W and X are oxygen.

18. The composition of claim 16, wherein the mixture comprises at least a first set of compounds in which k is 0 and $R^3$ is $C_6$ to $C_{22}$ alkyl and a second set of compounds in which k is 0 and $R^3$ is $C_6$ to $C_{22}$ alkyl, provided that $R^3$ differs in each of the two sets.

19. The composition of claim 16, wherein the mixture comprises at least a first set of compounds in which k is 1 and $R^3$ is $C_6$ to $C_{22}$ alkyl and a second set of compounds in which k is 1 and $R^3$ is $C_{16}$ to $C_{22}$ alkyl, provided that $R^3$ differs in each of the two sets.

20. The composition of claim 16, wherein the mixture comprises at least a first set of compounds in which k is 2 and $R^3$ is $C_6$ to $C_{22}$ alkyl and a second set of compounds in which k is 2 and $R^3$ is $C_6$ to $C_{22}$ alkyl, provided that $R^3$ differs in each of the two sets.

21. The composition of claim 16, wherein the mixture comprises at least a first set of compounds in which k is 0 and $R^3$ is $C_6$ to $C_{22}$ alkyl and a second set of compounds in which k is 1 and $R^3$ is $C_6$ to $C_{22}$ alkyl.

22. The composition of claim 16, wherein the mixture comprises at least a first set of compounds in which k is 0 and $R^3$ is $C_6$ to $C_{22}$ alkyl and a second set of compounds in which k is 2 and $R^3$ is $C_6$ to $C_{22}$ alkyl.

23. The composition of claim 16, wherein the mixture comprises at least a first set of compounds in which k is 1 and $R^3$ is $C_6$ to $C_{22}$ alkyl and a second set of compounds in which k is 2 and $R^3$ is $C_6$ to $C_{22}$ alkyl.

24. The composition of claim 16, wherein the mixture comprises at least a first set of compounds in which k is 0 and $R^3$ is $C_6$ to $C_{122}$alkyl, a second set of compounds in which k is 1 and $R^3$ is $C_6$ to $C_{22}$ alkyl, and a third set of compounds in which k is 2 and $R^3$ is $C_6$ to $C_{22}$ alkyl.

25. The composition of claim 14, wherein the composition has a critical micelle concentration (CMC) in water at 25° C. and atmospheric pressure.

26. The composition of claim 14, further comprising at least one agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a preservative, a coloring agent, a fragrance agent, and combinations thereof.

27. The composition of claim 14, wherein the composition is used in commercial or residential laundry products, industrial or household cleaning products, floor polishing products, personal care or cosmetic products, textile processing, metal processing, paper processing, agricultural applications, latex production, paper de-inking, or crude oil drilling applications.

28. A process for cleaning an article, the process comprising contacting the article with a composition comprising at least one compound comprising Formula (II):

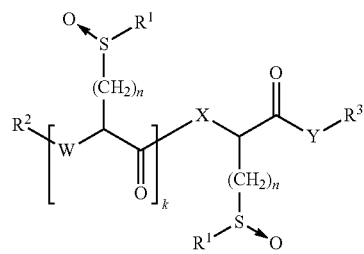

wherein:
$R^1$ is hydrocarbyl or substituted hydrocarbyl;
$R^2$ is H, hydrocarbyl, or substituted hydrocarbyl;
$R^3$ is hydrocarbyl or substituted hydrocarbyl having six or more carbon atoms in the principal chain;
W, X, and Y are independently O or NH;
n is an integer of 1 or greater; and
k is an integer of 0 or greater.

29. The process of claim 28, wherein $R^1$ is alkyl; $R^2$ is hydrogen, alkyl, acyl, $(CH_2CH_2O)_pH$, $(CH_2CH(CH_3)O)_pH$, or a combination of $(CH_2CH_2O)_pH$ and $(CH_2CH(CH_3)O)_pH$; p is an integer of 2 or greater; and $R^3$ is $C_6$ to $C_{30}$ alkyl.

30. The process of claim 29, wherein n is 2; $R^1$ is methyl; $R^2$ is hydrogen; $R^3$ is $C_6$ to $C_{22}$ alkyl; and W and X are oxygen.

31. The process of claim 30, wherein the composition comprises a mixture of compounds in which k is 0, 1, 2, 3, 4, or combinations thereof.

32. The compound of claim 7, wherein the CMC is less than about 1 mM.

33. The compound of claim 7, wherein the CMC is less than about 0.1 mM.

34. The compound of claim 12, wherein the CMC is less than about 1 mM.

35. The compound of claim 12, wherein the CMC is less than about 0.1 mM.

36. The composition of claim 25, wherein the CMC is less than about 1 mM.

37. The composition of claim 25, wherein the CMC is less than about 0.1 mM.

* * * * *